United States Patent
Ono et al.

(10) Patent No.: US 10,544,181 B2
(45) Date of Patent: Jan. 28, 2020

(54) SUGAR DERIVATIVE GELATORS

(71) Applicants: KYUSHU UNIVERSITY, Fukuoka-shi, Fukuoka (JP); Institute of Systems, Information Technologies and Nanotechnologies, Fukuoka-shi, Fukuoka (JP); NISSAN CHEMICAL INDUSTRIES, LTD., Tokyo (JP)

(72) Inventors: Fumiyasu Ono, Fukuoka (JP); Koichiro Saruhashi, Funabashi (JP); Osamu Hirata, Funabashi (JP); Seiji Shinkai, Fukuoka (JP); Tatsuhiro Yamamoto, Fukuoka (JP)

(73) Assignees: KYUSHU UNIVERSITY, Fukuoka-shi (JP); INSTITUTE OF SYSTEMS, INFORMATION TECHNOLOGIES AND NANOTECHNOLOGIES, Fukuoka-shi (JP); NISSAN CHEMICAL INDUSTRIES, LTD., Tokyo (JP)

( * ) Notice: Subject to any disclaimer, the term of this patent is extended or adjusted under 35 U.S.C. 154(b) by 94 days.

(21) Appl. No.: 15/755,393

(22) PCT Filed: Aug. 25, 2016

(86) PCT No.: PCT/JP2016/074860
§ 371 (c)(1),
(2) Date: Feb. 26, 2018

(87) PCT Pub. No.: WO2017/034004
PCT Pub. Date: Mar. 2, 2017

(65) Prior Publication Data
US 2018/0208618 A1    Jul. 26, 2018

(30) Foreign Application Priority Data

Aug. 25, 2015   (JP) ................... 2015-165951

(51) Int. Cl.
| | | |
|---|---|---|
| *C07H 9/04* | (2006.01) | |
| *A61K 8/60* | (2006.01) | |
| *C09K 3/00* | (2006.01) | |
| *A61K 47/26* | (2006.01) | |
| *A61Q 1/02* | (2006.01) | |
| *A61K 8/04* | (2006.01) | |
| *C07B 37/04* | (2006.01) | |
| *C07C 43/32* | (2006.01) | |
| *C07C 233/03* | (2006.01) | |

(52) U.S. Cl.
CPC ............... *C07H 9/04* (2013.01); *A61K 8/042* (2013.01); *A61K 8/60* (2013.01); *A61K 47/26* (2013.01); *A61Q 1/02* (2013.01); *C07B 37/04* (2013.01); *C09K 3/00* (2013.01); *C07C 43/32* (2013.01); *C07C 233/03* (2013.01)

(58) Field of Classification Search
None
See application file for complete search history.

(56) References Cited

U.S. PATENT DOCUMENTS 9,278,989 B2 *  3/2016  Ono .................. A61K 8/60

FOREIGN PATENT DOCUMENTS

| JP | H01-139520 A | 6/1989 | |
|---|---|---|---|
| JP | 2515261 B2 | 7/1996 | |
| JP | H11323309 A | 11/1999 | |
| WO | 2013/133419 A1 | 9/2013 | |
| WO | 2016/088076 A1 | 6/2016 | |
| WO | WO-2016130417 A1 * | 8/2016 | ............. A61K 45/06 |

OTHER PUBLICATIONS

Nov. 29, 2016 Written Opinion issued in International Patent Application No. PCT/JP2016/074860.
Shinkai et al. "Sugar-Integrated Gelators of Organic Solvents." Chemistry A European Journal, vol. 7, No. 20, pp. 4327-4334, 2001.
Gozlan et al. "Catalytic reductive cleavage of methyl α-D-glucoside acetals to ethers using hydrogen as a clean reductant." RSC Advances, vol. 4, pp. 50653-50661, 2014.

(Continued)

*Primary Examiner* — Traviss C McIntosh, III
(74) *Attorney, Agent, or Firm* — Oliff PLC

(57) ABSTRACT

A novel gelator including a sugar derivative; a gelator including a compound of Formula (1) or Formula (2):

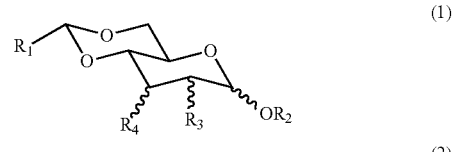

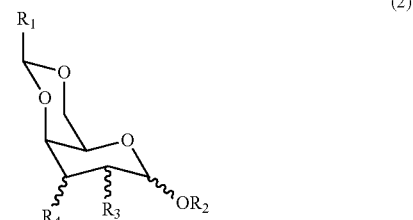

wherein $R_1$ is a linear or branched alkyl group having a carbon atom number of 9 to 20, a cyclic alkyl group having a carbon atom number of 13 to 20, or a linear or branched alkenyl group having a carbon atom number of 9 to 20, $R_2$ is a hydrogen atom, a linear or branched alkyl group having a carbon atom number of 1 to 10, or an aryl group optionally having a substituent, and $R_3$ and $R_4$ are hydroxy groups.

15 Claims, 4 Drawing Sheets

(56) References Cited

OTHER PUBLICATIONS

Dahlhoff et al. "Mesogenic 4-O-Alkyl-D-Glucoses via Methyl 4,6-O-Alkylidene-D-glucopyranosides." Liebigs annalen der chemie, vol. 10, No. 10, pp. 1063-1067, 1993.
Sadozai et al. "Synthesis of plasmalopsychosines A and B, two novel lysosphingolipids found in human brain." Carbohydrate Research, vol. 241, pp. 301-307, 1993.
Nov. 29, 2016 Search Report issued in International Patent Application No. PCT/JP2016/074860.
Jun. 18, 2018 Extended European Search Report issued in European Patent Application 16839351.0.

* cited by examiner (a)                (b)

(a)                    (b)

(a)                    (b)

(a)     (b)

(a)     (b)

(a)   (b)   (c)   (d)

SUGAR DERIVATIVE GELATORS

TECHNICAL FIELD

The present invention relates to a novel gelator and, in particular, relates to a novel gelator including an alkyl-sugar derivative.

BACKGROUND ART

A structure that contains a fluid in a three-dimensional network structure formed by a substance having gel forming ability (hereinafter, referred to as a gelator) is referred to as a gel. Generally, the case where the fluid is water is referred to as a hydrogel and the case where the fluid is an organic liquid other than water (organic solvent, oil, and the like) is referred to as an organogel or an oil gel. The oil gel (organogel) is used for adjusting flowability of cosmetics and paints in the field of cosmetics, pharmaceutical products, agricultural chemicals, foods, adhesives, paints, resins, and the like. The oil gel (organogel) is also widely used for the field of environmental protection such as preventing water pollution by forming the gel of waste oil as a solid.

Research of the gelator has been mainly carried out for macromolecular compounds. In recent years, however, research and development have been carried out for low molecular-weight compounds to which various functions can be easily introduced compared with the macromolecular compounds. As described above, the oil gel (organogel) has been used in a wide range of fields and has been expected to expand its field of use in the future. Consequently, for expanding the use of the oil gel, the gelator of the low molecular-weight compound (hereinafter, may be referred to as a low molecular-weight gelator) is required to have gel forming ability to a wide variety of organic solvents. To these problems, until now, various compounds have been developed as the low molecular-weight gelator that can form a gel having excellent stability with a small added amount to various organic solvents. As one of the compounds, for example, it has been reported that a sugar derivative derived from each of monosaccharides has a structure easy to form a strong hydrogen bond with each other and thus that the sugar derivative can form the gels of various types of organic solvents (Non Patent Document 1). It has been reported that the low molecular-weight gelator using the sugar derivative can gel both solvents of water and oil (hydrophilic organic solvent and hydrophobic organic solvent) and a mixed solvent thereof (Patent Document 1).

PRIOR ART DOCUMENTS

Patent Document

Patent Document 1: WO 2013/133419 Pamphlet

Non Patent Document

Non Patent Document 1: S. Shinkai et al., Chem. Eur. J. 2001, 7, No 20, 4327-4334

SUMMARY OF THE INVENTION

Problems to be Solved by the Invention

Until now, a gelator for oil made of a low molecular-weight compound for nonaqueous media such as organic solvents has been developed. However, a problem of limitation of media that can form a gel and other problems arise. Therefore, for creating a novel oil gel having novel uses and functions, development of a novel low molecular-weight gelator for oil gels that can form the gels of various media has been sought.

The above gelator of the sugar derivative can form the gels of various types of solvents by changing the types of sugars. Gelation of a wide variety of solvents using one kind of sugar derivative is relatively difficult. The gel obtained using the sugar derivative described in Non Patent Document 1 has no preservation stability. The gelator disclosed in Patent Document 1 can form the gel of the mixed solvent of water and oil (hydrophilic organic solvent and hydrophobic organic solvent). The gelator, however, involves costs for safety tests including phototoxicity.

As described above, the gelator that can form the gel of the mixed solvent of water and oil (hydrophobic organic solvent) to form a water/oil dispersion gel, that is, an emulsion gel (gel emulsion) is particularly useful for cosmetics and medical base materials that require high bio-safety. However, a revolutionary gelator that secures gelation ability to a wide variety of solvents and bio-safety has not yet been developed.

Generally, for cosmetic applications and the like, O/W (oil-in-water type) emulsions have light spread on skin and weak oily feeling and thus have been applied to many cosmetics until now. On the other hand, W/O (water-in-oil type) emulsions give oilier feeling when applied to the skin as compared with the O/W emulsions. The W/O emulsions, however, are suitable for applications to which water resistance (perspiration resistance) is required and the effects of makeup can be sustained for a long time. It can be also expected that the W/O emulsions can achieve refreshing feeling of use by increasing the water content of the dispersed phase (internal phase).

Therefore, in recent years, the demand for a gelator that can provide the emulsion gel as the W/O emulsion gel has been also increased.

The present invention has been made based on the above circumstances. An object achieved by solving the above problems is to provide a novel gelator that can form the gels of various kinds of organic solvents, can independently form not only the gel of water, the hydrophilic organic solvent, and the hydrophobic organic solvent (oil and the like) but also the gel of the mixed solvent thereof, particularly the mixed solvent of water and the hydrophobic organic solvent (oil), can prepare gels having excellent bio-safety, and in addition, can prepare the W/O emulsion gels.

Means for Solving the Problems

As a result of extensive research to solve the above problems, the inventors of the present invention have found that when an alkyl-sugar derivative is applied as a gelator, surprisingly, the alkyl-sugar derivative can form the gels to various solvents, in particular, can form the gel of the mixed solvent of water and hydrophobic solution (oil), and thus have completed the present invention.

More specifically, the present invention relates to, as a first aspect, a gelator comprising a compound of Formula (1) or Formula (2):

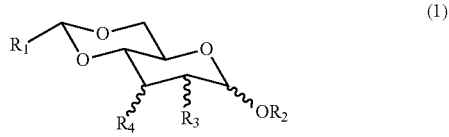

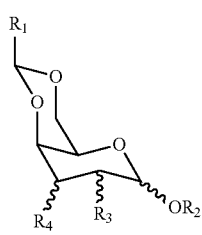

(2)

[wherein $R_1$ is a linear or branched alkyl group having a carbon atom number of 9 to 20, a cyclic alkyl group having a carbon atom number of 13 to 20, or a linear or branched alkenyl group having a carbon atom number of 9 to 20;

$R_2$ is a hydrogen atom, a linear or branched alkyl group having a carbon atom number of 1 to 10, or an aryl group optionally having a substituent; and $R_3$ and $R_4$ are hydroxy groups].

The present invention relates to, as a second aspect, the gelator according to the first aspect, in which the compound of Formula (1) is a compound of Formula (3):

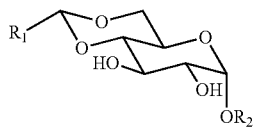

(3)

[wherein $R_1$ and $R_2$ have the same meanings as defined in Formula (1)].

The present invention relates to, as a third aspect, the gelator according to the first aspect, in which the compound of Formula (1) is a compound of Formula (4):

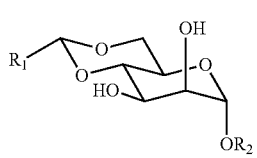

(4)

[wherein $R_1$ and $R_2$ have the same meanings as defined in Formula (1)].

The present invention relates to, as a fourth aspect, a gel comprising:

the gelator according to any one of the first to third aspects; and a hydrophobic organic solvent, a hydrophilic organic solution, a hydrophobic organic solution, or an aqueous solution.

The present invention relates to, as a fifth aspect, a gel comprising:

the gelator according to any one of the first to third aspects;

a surfactant; and a hydrophobic organic solvent, a hydrophilic organic solvent, water, a hydrophilic organic solution, a hydrophobic organic solution, or an aqueous solution.

The present invention relates to, as a sixth aspect, the gel according to the fourth aspect or the fifth aspect, in which the hydrophobic organic solvent is at least one solvent selected from the group consisting of vegetable oils, esters, silicone oils, and hydrocarbons.

The present invention relates to, as a seventh aspect, the gel according to the fourth aspect or the fifth aspect, in which the hydrophobic organic solution is a mixed solvent of the hydrophobic organic solvent according to the sixth aspect and water.

The present invention relates to, as an eighth aspect, the gel according to the fifth aspect, in which the hydrophilic organic solvent is at least one solvent selected from the group consisting of methanol, ethanol, 2-propanol, i-butanol, pentanol, hexanol, 1-octanol, iso-octanol, acetone, cyclohexanone, acetonitrile, dioxane, glycerol, propylene glycol, ethylene glycol, and dimethyl sulfoxide.

The present invention relates to, as a ninth aspect, the gel according to the fourth aspect or the fifth aspect, in which the hydrophilic organic solution is a mixed solvent of the hydrophilic organic solvent according to the eighth aspect and water.

The present invention relates to, as a tenth aspect, the gel according to any one of the fourth to ninth aspects, in which fine particles are further dispersed in the gel.

The present invention relates to, as an eleventh aspect, the gelator according to any one of the first to third aspects, in which the gelator is a gelator of an ionic liquid. The present invention relates to, as a twelfth aspect, a gel comprising:

the gelator according to any one of the first to third aspects, and an ionic liquid.

The present invention relates to, as a thirteenth aspect, a cosmetic base material or a medical base material comprising the gelator according to any one of the first to third aspects.

The present invention relates to, as a fourteenth aspect, a method for producing the compound of Formula (1) or Formula (2) according to the first aspect, the method being characterized by comprising:

producing the compound of Formula (1) or Formula (2) by annelation reaction of a compound of a formula $R_1$—CHO (wherein $R_1$ is a linear or branched alkyl group having a carbon atom number of 9 to 20, a cyclic alkyl group having a carbon atom number of 13 to 20, or a linear or branched alkenyl group having a carbon atom number of 9 to 20) with glucose, mannose, galactose, or a derivative thereof in a single pot in the presence of DMF, triethyl orthoformate, or p-toluenesulfonic acid.

The present invention relates to, as a fifteenth aspect, a gelator comprising a compound of Formula (7) or Formula (8):

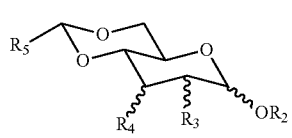

(7)

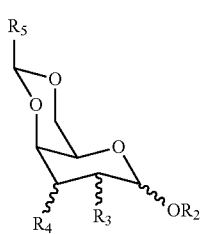

(8)

[wherein

R₅ is a linear or branched alkyl group having a carbon atom number of 13 to 20, a cyclic alkyl group having a carbon atom number of 13 to 20, or a linear or branched alkenyl group having a carbon atom number of 13 to 20;

R₂ is a hydrogen atom, a linear or branched alkyl group having a carbon atom number of 1 to 10, or an aryl group optionally having a substituent; and R₃ and R₄ are hydroxy groups].

Effects of the Invention

The gelator of the present invention has gel forming ability to various solvents such as water and oil (hydrophobic organic solvent). For example, the gelator of the present invention can form the gels of various systems such as the mixed hydrophilic solvent of water and the hydrophilic organic solvent, and the hydrophobic organic solvent (oil) and can provide gels having excellent thixotropy.

In particular, the gelator of the present invention can form water/oil dispersion gels from the mixed solvent of water and oil (hydrophobic organic solvent), can form W/O emulsion gels having a high water content, and can provide the water/oil dispersion gels providing excellent feeling of use.

The gelator of the present invention can form the gel of an ionic liquid and can form an ionic liquid-oil dispersion gel (gel emulsion) from a mixed solvent of the ionic liquid and oil.

The gelator of the present invention can form a gel in a system containing fine particles and can form a water/oil dispersion gel from the mixed solvent of water and oil (hydrophobic organic solvent) containing the fine particles.

The gelator of the present invention is prepared from a monosaccharide such as glucose, mannose, galactose, or a derivative thereof as a raw material and thus not only has high bio-safety but also can keep raw material cost remarkably low.

According to the production method of the present invention, the above gelator can be produced from the derivatives of glucose, mannose, and galactose in a single pot and a compound that can provide an inexpensive gelator can be easily produced. The method does not require methanol or a metal catalyst at the time of production. Consequently, a compound that can exclude the residual of such stimulus compound from the system after the reaction and is suitable as the gelator for the base material requiring high safety such as a cosmetic base material, a medical base material, and a food base material can be produced.

MODES FOR CARRYING OUT THE INVENTION

[Gelator]

Figure 1:
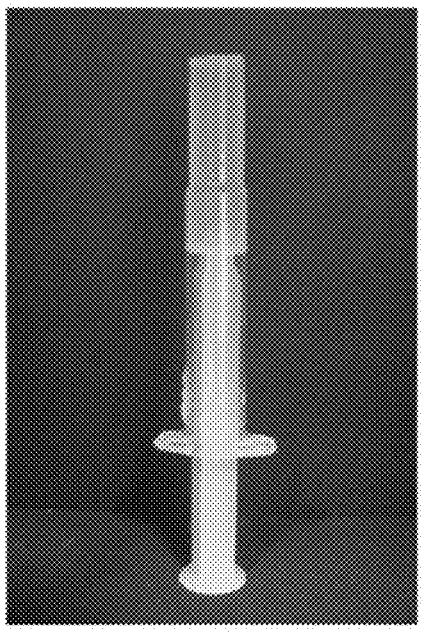
FIG. 1 is a photograph of KF995 gel prepared in Example 2 by blending 2 wt % of a glucose derivative: Compound [8].

The gelator of the present invention includes a compound of Formula (1) or Formula (2).

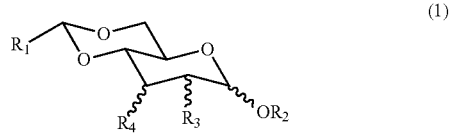

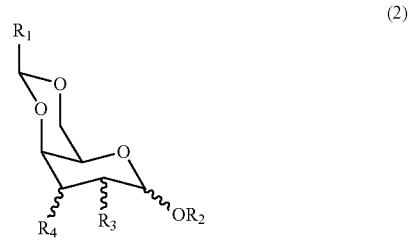

[wherein

R₁ is a linear or branched alkyl group having a carbon atom number of 9 to 20, a cyclic alkyl group having a carbon atom number of 13 to 20, or a linear or branched alkenyl group having a carbon atom number of 9 to 20;

R₂ is a hydrogen atom, a linear or branched alkyl group having a carbon atom number of 1 to 10, or an aryl group optionally having a substituent; and R₃ and R₄ are hydroxy groups].

Examples of the linear or branched alkyl group having a carbon atom number of 9 to 20 include nonyl group, decyl group, tridecyl group, tetradecyl group, pentadecyl group, hexadecyl group, heptadecyl group, octadecyl group, nonadecyl group, and eicosyl group and groups formed by branching these groups.

Examples of the cyclic alkyl group having a carbon atom number of 13 to 20 include not only a group formed of a cyclic alkyl group alone (for example, cyclotridecyl group, cyclotetradecyl group, cyclopentadecyl group, cyclohexadecyl group, cycloheptadecyl group, cyclooctadecyl group, cyclononadecyl group, a cycloeicosyl group) but also a linear and/or branched alkyl groups having a cyclic structure such as a cyclopentyl ring and a cyclohexyl ring and having a carbon atom number of 13 to 20.

Examples of the linear or branched alkenyl group having a carbon atom number of 9 to 20 include nonenyl group, decenyl group, tridecenyl group, tetradecenyl group, pentadecenyl group, hexadecenyl group, heptadecenyl group, octadecenyl group, nonadecenyl group, and eicosenyl group and groups formed by branching these groups.

Examples of the linear or branched alkyl group having a carbon atom number of 1 to 10 include methyl group, ethyl group, n-propyl group, n-butyl group, n-pentyl group, n-hexyl group, n-heptyl group, n-octyl group, n-nonyl group, n-decyl group, isopropyl group, isobutyl group, sec-butyl group, tert-butyl group, and 2-ethylhexyl group.

Examples of the aryl group include phenyl group, benzyl group, 1-naphthyl group, 2-naphthyl group, 1-anthryl group, and 1-phenanthryl group. The aryl group optionally has a substituent and examples of such a substituent include a linear, branched, or cyclic alkyl group that optionally includes an ester bond, an amide bond, or an ether bond and a halogen atom.

In Formula (1) or (2), $R_2$ is preferably a hydrogen atom, methyl group, or ethyl group from the viewpoint of favorably forming the gels of various solvents described below using the gelator of the present invention. Among these groups, a hydrogen atom or methyl group is preferable.

$R_1$ may be, for example, a group having a carbon atom number of 13 or more or a group having a carbon atom number of 15 or more. However, from the viewpoint that a gel with high transparency and uniformity without releasing a solvent can be obtained when the gelator is mixed with various solvents described below singly or in combination, $R_1$ is preferably a linear alkyl group having a carbon atom number of 17 or more. A gel of a hydrophilic organic solution including the hydrophilic organic solvent in a high ratio can be formed by increasing the number of carbon atoms (lengthening the carbon chain length) of $R_1$.

The compound of Formula (1) or (2) can be obtained by known methods, for example, by reacting an aldehyde having the $R_1$ group with a monosaccharide.

The monosaccharide that can be used is not particularly limited as long as the monosaccharide has a pyranose ring structure and examples of the monosaccharide include allose, altrose, glucose, mannose, gulose, idose, galactose, and talose.

Among them, glucose, mannose, and galactose are preferable as the monosaccharides from the viewpoint that these monosaccharides are relatively inexpensive and particularly expected for biocompatibility. Among these monosaccharides, glucose and mannose are preferable.

Among the compounds of Formula (1) or (2), a compound of Formula (3) having a glucose moiety or a compound of Formula (4) having a mannose moiety is particularly preferable.

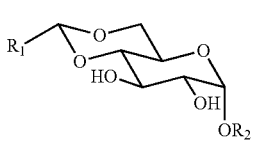

(3)

[wherein $R_1$ and $R_2$ have the same meanings as defined in Formula (1)]

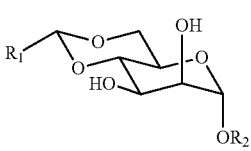

(4)

[wherein $R_1$ and $R_2$ have the same meanings as defined in Formula (1)]

Among the compounds of Formula (3), a compound of Formula (5) is preferable.

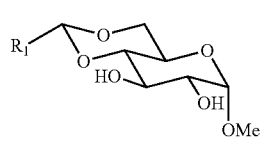

(5)

[wherein $R_1$ has the same meanings as defined in Formula (1)]

Among the compounds of Formula (4), a compound of Formula (6) is preferable.

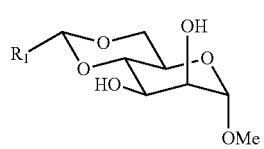

(6)

[wherein $R_1$ has the same meanings as defined in Formula (1)]

The compound of Formula (3) (glucose type gelator) has the greatest characteristic in that the compound has gel forming ability in both hydrophilic organic solution and the oil (hydrophobic organic solvent) and, in particular, can form water/oil dispersion gels to the mixed solvent of water/oil.

The compound of Formula (3) can provide a gel having excellent thixotropy. The compound of Formula (3) also has characteristic in that the compound can form a self-sustainable (having a self-supporting property) gel having transparency.

Among the compounds of Formula (1) or Formula (2), a compound in which $R_1$ is the linear or branched alkyl group having a carbon atom number of 13 to 20, the cyclic alkyl group having a carbon atom number of 13 to 20, or the linear or branched alkenyl group having a carbon atom number of 13 to 20, that is, a compound of Formula (7) or Formula (8) is also an object of the present invention.

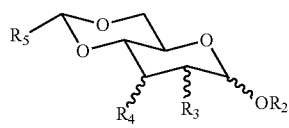

(7)

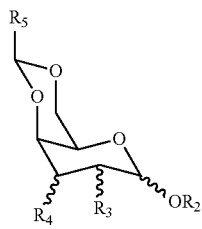

(8)

[wherein

R$_5$ is a linear or branched alkyl group having a carbon atom number of 13 to 20, a cyclic alkyl group having a carbon atom number of 13 to 20, or a linear or branched alkenyl group having a carbon atom number of 13 to 20;

R$_2$ is a hydrogen atom, a linear or branched alkyl group having a carbon atom number of 1 to 10, or an aryl group optionally having a substituent; and R$_3$ and R$_4$ are hydroxy groups].

[Gel]

The gel of the present invention can be obtained by forming the gel of the solvent with the gelator. Specifically, a production method in which a predetermined amount of the gelator is dissolved in a solvent by heating and the resultant mixture is cooled is exemplified. Usually, complete dissolution of the gelator is preferable when the gelator is dissolved by heating.

In this specification, gelation (or forming a gel) means that a liquid having fluidity becomes in a state of losing fluidity.

At the time of forming the gel of the solvent, the amount of the gelator of the present invention to be used is not particularly limited as long as the gelator provides the effect of the present invention. Usually, the amount is 0.001% by mass to 20% by mass, for example, 0.02% by mass to 5% by mass relative to the mass of the solvent in which the gel is formed.

The solvent is not particularly limited as long as the solvent does not prevent gelation. Preferable specific examples of the solvent may include a hydrophobic organic solvent, a hydrophilic organic solvent, water, a mixed solvent of water and a hydrophilic organic solvent (referred to as a hydrophilic organic solution in this specification), a mixed solvent of a hydrophobic organic solvent and water (referred to as a hydrophobic organic solution in this specification), or an aqueous solution in which an organic acid or an inorganic acid is dissolved in water or an inorganic salt or an organic salt is dissolved in water (referred to as an aqueous solution in this specification).

The gel of the present invention may be formed by including the gelator and the hydrophobic organic solvent, the hydrophilic organic solution, a hydrophobic organic solution, or an aqueous solution. Alternatively, the gel of the present invention may be formed by including the gelator, a surfactant, and the hydrophobic organic solvent, the hydrophilic organic solvent, water, the hydrophilic organic solution, the hydrophobic organic solution, or the aqueous solution.

Preferable specific examples of the hydrophobic organic solvent include vegetable oils such as olive oil, coconut oil, castor oil, jojoba oil, or sunflower oil; esters such as ethyl acetate, cetyl octanoate, isopropyl myristate, or isopropyl palmitate; hydrocarbons such as toluene, xylene, n-hexane, cyclohexane, octane, squalane, squalene, mineral oils, silicone oils, or hydrogenated polyisobutenes, and halogenated hydrocarbons such as chloroform.

Among them, as the hydrophobic organic solvent, olive oil, isopropyl myristate, toluene, cyclohexane, squalane, squalene, silicone oils such as linear silicone, cyclic silicone, alkyl modified silicone, phenyl modified silicone, dimethicone, or dimethiconol, and octane are preferable.

As the silicone oil, a linear silicone (trade name: 2-1184), cyclic silicones (decamethylcyclopentasiloxane (trade name: SH245) and the like), an alkyl-modified silicone (trade name: SS-3408), a phenyl-modified silicone (trade name: PH-1555), a dimethicone (trade name: BY-11-0 series), and a dimethiconol (trade name: CB-1556), or the like available from Dow Corning Toray Co., Ltd. or decamethylcyclopentasiloxane (trade name: KF995) available from Shin-Etsu silicone Co. may be used.

The hydrophilic organic solvent means an organic solvent that dissolves in water at any ratio and examples of the hydrophilic organic solvent include alcohols, acetone, cyclohexanone, acetonitrile, dioxane, glycerol, and dimethylsulfoxide.

The alcohols are preferably water-soluble alcohols that are freely soluble in water, more preferably $C_{1-9}$ alcohols, polyhydric alcohols, higher alcohols, and glycerides.

Specific examples of the $C_{1-9}$ alcohols include methanol, ethanol, 2-propanol, i-butanol, pentanol, hexanol, 1-octanol, and isooctanol. Specific examples of the polyhydric alcohols include ethylene glycol, propylene glycol, and polypropylene glycols. Specific examples of higher alcohols include octyldodecanol, stearyl alcohol, and oleyl alcohol. Specific examples of the glycerides include trioctanoin, tri(caprylcaprylic acid) glyceryl, and glyceryl stearate.

Among them, as the hydrophilic organic solvent, methanol, ethanol, 2-propanol, i-butanol, pentanol, hexanol, 1-octanol, isooctanol, acetone, cyclohexanone, acetonitrile, dioxane, glycerol, propylene glycol, ethylene glycol, and dimethyl sulfoxide are preferable and, glycerol, propylene glycol, and ethylene glycol are more preferable.

The organic acid or inorganic acid used in the aqueous solution may be used singly or in combination of two or more of them.

Examples of preferable organic acids include acetic acid, citric acid, succinic acid, lactic acid, malic acid, maleic acid, fumaric acid, and trifluoroacetic acid. Acetic acid, citric acid, succinic acid, lactic acid, and malic are more preferable and acetic acid, citric acid, and lactic acid are further preferable.

Examples of the preferable inorganic acids include hydrochloric acid, phosphoric acid, carbonic acid, sulfuric acid, nitric acid, and boric acid. Hydrochloric acid, phosphoric acid, carbonic acid, and sulfuric acid are more preferable and hydrochloric acid, phosphoric acid, and carbonic acid are further preferable.

As the inorganic salt or the organic salt used for the aqueous solution, plural kinds of the inorganic salt or the organic salt may be used. One or two kinds of the inorganic salt or the organic salt, however, are preferably used. Having buffering ability of the aqueous solution by adding two kinds of salts is also desirable.

Examples of the preferable inorganic salts include inorganic carbonates, inorganic sulfates, inorganic phosphates, and inorganic hydrogenphosphates. Calcium carbonate, sodium carbonate, potassium carbonate, sodium sulfate, potassium sulfate, magnesium sulfate, potassium phosphate, sodium phosphate, disodium hydrogen phosphate, or sodium dihydrogen phosphate are more preferable. Calcium carbonate, magnesium sulfate, disodium hydrogen phosphate, or sodium dihydrogen phosphate are further preferable.

Examples of the preferable organic salts include inorganic salts of organic acids such as inorganic acetate, inorganic lactate, and inorganic citrate, hydrochlorides of organic amines, or organic amine acetates. Sodium acetate, potassium acetate, sodium lactate, potassium lactate, sodium citrate, potassium citrate, ethylenediamine hydrochloride, ethylenediamine tetraacetate, and trishydroxymethylaminomethane hydrochloride are more preferable.

The gelator of the present invention can be used in an amount of 0.001% mass to 20% by mass or 0.001% by mass to 10% by mass, preferably 0.05% by mass to 10% by mass or 0.1% by mass to 10% by mass, for example, 0.02% by mass to 5% by mass or 0.1% by mass to 5% by mass relative to the above hydrophobic organic solvent, hydrophilic organic solvent, water, hydrophilic organic solution, hydrophobic organic solution, or aqueous solution being the medium.

A gel can be obtained by adding the gelator of the present invention to the above hydrophobic organic solvent, hydrophilic organic solvent, water, hydrophilic organic solution, hydrophobic organic solution, or aqueous solution being the medium, dissolving the gelator by heating and stirring if required, and thereafter allowing the resultant mixture to stand at room temperature. Gel strength can be controlled by the concentration of the gelator.

The gel formed with the gelator of the present invention may be mixed with various additives (organic compounds such as surfactants, ultraviolet absorbers, moisturizing agents, preservative agents, antioxidants, perfumes, and physiologically active substances (medicinal components) and inorganic compounds such as titanium oxide, talc, mica, and water) depending on needs such as applications as long as the additives do not inhibit the gelation ability of the gelator.

Examples of the surfactants include nonionic surfactants such as Tween 20, Span 80, and sucrose sugar esters, various anionic surfactants, and various cationic surfactants.

Examples of the physiologically active substances include L-ascorbic acid, L-ascorbic acid 2-phosphate trisodium salt (a vitamin C derivative), glycine, and glucosamine.

[Fine Particles]

The gel of the present invention may be in the form of further including fine particles dispersed therein.

The fine particles refer to remarkably minute particles and may have a spherical shape or may have a shape having different values of longitudinal, transversal, and height. The number average particle diameter of the particles is preferably 0.1 nm to 20 μm and more preferably 1 nm to 2,000 nm.

The fine particles usable in the present invention are inorganic or organic fine particles. Examples of the inorganic particles include titanium oxide, zinc oxide, chromium oxide, black iron oxide, red iron oxide, yellow iron oxide, red lead, black titanium oxide, chromium hydroxide, lithium cobalt titanate, cobalt blue, turquoise, titanium yellow, Fe—Zn—Cr-based brown, Cu—Cr-based black, alumina, cadmium yellow, cadmium red, yellow lead green, chromium vermillion, zinc chromate, manganese violet, ultramarine blue, iron blue, calcium phosphate, hydroxyapatite, calcium carbonate, magnesium carbonate, barium sulfate, aluminum powder, bronze powder, carbon black, bismuth oxychloride, mica titanium, lead white, barium titanate, lead zirconate titanate, ferrite, forsterite, zirconia, zircon, mullite, steatite, coatierite, aluminum nitride, silicon nitride, kaolin, anhydrous silicic acid, magnesium aluminum silicate, synthetic phlogopite, sericite, talc, and mica. Examples of the organic particles include linen cellulose powder, wheat starch, silk powder, corn starch, aluminum stearate, zinc stearate, magnesium stearate, calcium stearate, zinc palmitate, zinc myristate, magnesium myristate, zinc undecylenate, silicon carbide, cellulose powder, polyethylene powder, nylon powder, alkyl polyacrylates, crosslinked polystyrenes, methylsiloxane network polymers, polyurethanes, Lake Red C, Brilliant Carmine 6B, Lionol Red 498, Lionol Yellow K-5G, Lithol Rubine B, Permanent Red 4R, Naphthol Red, First Yellow G, Disazo Yellow HR, Pyrazolone Orange, Benzimidazolone Carmine HF4C, Benzimidazolone Yellow H3Q Condensed Azo Red BR, Condensed Azo Yellow GR, Phthalocyanine Blue, Phthalocyanine Green, Diantranquinonyl Red, Thioindigo Bordeaux, Perylene Orange, Perylene Red, Quinacridone Magenta, Dioxazine Violet, Quinophthalone Yellow, Azomethine Yellow, Isoindolinone Yellow G, Diketopyrrole Red, Rhodamine B, Rhodamine 6G Lake, and Quinoline Yellow Lake. When the materials are present as the fine particles, the materials and the like are not particularly limited and mixtures or composites thereof may be used. In consideration of scattering properties and shielding properties against light and durability as color materials, the fine particles may be metal oxides, mixtures thereof, or composites thereof.

When the fine particles are blended into the gel of the present invention, as a method for dispersing the fine particles, a mechanical dispersion treatment may be used together in order to further enhance the dispersion effect of the fine particles to cope with dispersion of various kinds of fine particles. Here, the mechanical dispersion treatment refers to treatment in which physical force such as impact or shearing is applied to aggregated particles to loose and disperse the aggregate. Examples of the mechanical dispersion treatment include a method of deforming and disintegrating the aggregated particles by disappearance of cavities caused by a generated sparse and dense state and expansion, which is utilized in an ultrasonic bath or an ultrasonic homogenizer, a method of utilizing a strong shearing force or impact force generated in a fine gap between the rotating blade and the stationary ring, which is utilized in a high speed homomixer or a colloid mill, a method of utilizing high-speed collision of the aggregated particles, which is utilized in a high-pressure homogenizer, and a method of dispersing the aggregated particles using collision, shearing, impact, friction, and the like with a medium, which is utilized in a bead mill. The mechanical dispersion treatment, however, is not limited to these methods.

When the fine particles are blended, the amount to be blended is not particularly limited as long as the fine particles are uniformly dispersed. The amount is preferably 0.1% by mass to 20% by mass (w/v %) and further preferably 0.5% by mass to 10% by mass (w/v %) relative to the volume of the fluid desired to form a gel.

[Various Applications]

As described above, the gelator of the present invention can form the gels of various solvents and can also form the gel of the mixed solvent of water and oil. Therefore, the gelator of the present invention and the gel obtained therefrom can be used for material in various fields such as a cosmetic base materials or a medical base material, a gel electrolyte, a base material for cell culture, a base material for preservation of biomolecules such as cells and proteins, an external base material, a base material for biochemistry, a base material for food, a contact lens, a paper diaper, an artificial actuator, and a base material for dry ground agriculture. The gelator of the present invention and the gel obtained therefrom can be also widely used for research, medical treatment, analysis, and various industries as a bioreactor carrier used for, for example, enzymes.

[Cosmetic Base Material or a Medical Base Material]

The cosmetic base material or medical base material of the present invention includes the gelator.

In addition to the gelator, the cosmetic base material or medical base material of the present invention may include water, an alcohol, a polyhydric alcohol, a hydrophilic organic solvent, a hydrophobic organic solvent, or a mixed solution thereof. As the alcohol, the polyhydric alcohol, the hydrophilic organic solvent, and the hydrophobic organic solvent, the exemplified compounds of the above alcohols, polyhydric alcohols, hydrophilic organic solvents, and hydrophobic organic solvents are included.

The cosmetic base material or medical base material of the present invention can include additive components such as physiologically active substances and functional substances generally blended to the cosmetic base material or the medical base material. Examples of such additive components include oily base materials, moisturizers, touch improvers, surfactants, polymers, thickening/gelators, solvents, propellants, antioxidants, reducing agents, oxidizing agents, preservative agents, antimicrobe agents, bactericides, chelating agents, pH adjusters, acids, alkalis, powder, inorganic salts, ultraviolet absorbers, whitening agents, vitamins and derivatives thereof, agents for hair growth, blood circulation accelerators, stimulants, hormones, anti-wrinkle agents, anti-aging agents, tightening agents, cold sensing agents, warm sensing agents, wound healing promoters, irritation mitigators, analgesics, cell activators, plant/animal/microbe extracts, antipruritic agents, corneum releasing/dissolving agents, antiperspirants, refrigerants, astringent agents, enzymes, nucleic acids, perfumes, coloring matters, colorants, dyes, pigments, antiphlogistic agents, antiinflammatory agents, antiasthmatic agents, anti-chronic obstructive pulmonary disease agents, antiallergic agents, immunomodulators, anti-infectious disease agents, and antifungal agents.

The cosmetic base material or medical base material of the present invention may include the gelator and at least one macromolecular compound.

Examples of the macromolecular compound include gelatin, sodium alginate, propylene glycol alginate, gum arabic, polyvinyl alcohols, polyacrylic acids, sodium polyacrylates, carboxymethyl cellulose, gellan gum, xanthan gum, carrageenan, polystyrenes, polymethyl methacrylates, polyvinyl pyrrolidones, polyethylene oxides, polylactic acids, polystyrene sulfonic acids, polyacrylonitriles, polyethylenes, and polyethylene terephthalates.

These additive components will be exemplified. Preferable examples of the oily base materials include higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diol; aralkyl alcohols and derivatives thereof such as benzyl alcohol; higher fatty acids such as lauric acid, myristic acid, palmitic acid, stearic acid, isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-heneicosanoic acid, long-chain branched fatty acids, dimeric acid, and hydrogenated dimeric acid, and metal soaps such as an aluminum salt, a calcium salt, a magnesium salt, a zinc salt, a potassium salt, and a sodium salt of the above higher fatty acids, and nitrogen-containing derivatives of the above higher fatty acids such as an amide of the above higher fatty acids; hydrocarbons such as liquid paraffins (mineral oil), heavy liquid isoparaffins, light liquid isoparaffins, an α-olefin oligomers, polyisobutenes, hydrogenated polyisobutenes, polybutenes, squalane, squalane derived from olive, squalene, vaseline, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch wax, polyethylene wax, and ethylene-propylene copolymers; vegetable oils and fats such as coconut oil, palm oil, palm kernel oil, safflower oil, olive oil, castor oil, avocado oil, sesame oil, tea seed oil, evening primrose oil, wheat germ oil, macadamia nut oil, hazelnut oil, candlenut oil, rose hip oil, meadowfoam oil, persic oil, tea tree oil, peppermint oil, corn oil, rapeseed oil, sunflower oil, wheat germ oil, linseed oil, cotton seed oil, soybean oil, peanut oil, rice bran oil, cacao butter, shea butter, hydrogenated coconut oil, hydrogenated castor oil, jojoba oil, and hydrogenated jojoba oil; animal oils and fats such as beef tallow, milk fat, horse fat, egg yolk oil, mink oil, and turtle oil; animal waxes such as spermaceti wax, lanolin, and orange roughy oil; lanolins such as liquid lanolin, reduced lanolin, adsorptively purified lanolin, lanolin acetate, acetylated lanolin, hydroxylated lanolin, polyoxyethylene lanolins, lanolin fatty acid, hard lanolin fatty acid, lanolin alcohol, acetylated lanolin alcohol, and an acetic acid (cetyl-lanolyl) ester; phospholipids such as lecithin, phosphatidylcholine, phosphatidyl ethanolamine, phosphatidylserine, phosphatidylglycerol, phosphatidylinositol, sphingophospholipids such as sphingomyelin, phosphatidic acid, and lysolecithin; phospholipid derivatives such as hydrogenated soybean phospholipid, partially hydrogenated soybean phospholipid, hydrogenated egg yolk phospholipid, and partially hydrogenated egg yolk phospholipid; sterols such as cholesterol, dihydrocholesterol, lanosterol, dihydrolanosterol, phytosterol, and cholic acid; sapogenins; saponins; sterol esters such as cholesteryl acetate, cholesteryl nonanoate, cholesteryl stearate, cholesteryl isostearate, cholesteryl oleate, di(cholesteryl/behenyl/octyldodecyl)N-lauroyl-L-glutamate, di(cholesteryl/octyldodecyl) N-lauroyl-L-glutamate, di(phytosteryl/behenyl/octyldodecyl)N-lauroyl-L-glutamate, di(phytosteryl/octyldodecyl)N-lauroyl-L-glutamate, acylsarcosine alkyl esters such as isopropyl N-lauroylsarcosinate, cholesteryl 12-hydroxystearate, macadamia nut oil fatty acid cholesteryl, macadamia nut oil fatty acid phytosteryl, phytosteryl isostearate, soft lanolin fatty acid cholesteryl, hard lanolin fatty acid cholesteryl, long-chain branched fatty acid cholesteryl, and long-chain α-hydroxy fatty acid cholesteryl; lipid complexes such as phospholipid-cholesterol complex and phospholipid-phytosterol complex; monoalcohol carboxylic acid esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentananoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid isopropyl, diethyl sebacate, diisopropyl sebacate, dioctyl sebacate, diisopropyl adipate, dibutyloctyl sebacate, diisobutyl adipate, dioctyl succinate, and triethyl citrate; oxy acid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, glyceryl tri(caprylate/caprinate), glyceryl tri(caprylate/caprinate/myristate/stearate), hydrogenated rosin triglyceride (hydrogenated ester gum), rosin triglyceride (ester gum), glyceryl behenate/eicosanedioate, trimethylolpropane trioctanoate, trimethylolpropane triisostearate, neopentyl glycol dioctanoate, neopentyl glycol dicaprinate, 2-butyl-2-ethyl-1,3-propanediol dioctanoate, propylene glycol dioleate, pentaerythrityl tetraoctanoate, hydrogenated rosin pentaerythrityl, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearates, polyglyceryl-10 nonaisostearates, polyglyceryl-8 deca(erucate/isostearate/ricinoleate)s, diglyceryl oligoester of (hexyldecanoic acid/sebacic acid), glycol distearate (ethylene glycol distearate), 3-methyl-1,5-pentanediol dineopentanoate, and 2,4-diethyl-1,5-pentanediol dineopentanoate; derivatives of dimer acids or dimer diols such as diisopropyl dimer-dilinoleate, diisostearyl dimer-dilinoleate, di(isostearyl/phytosteryl) dimer-dilinoleate, (phytosteryl/behenyl) dimer-dilinoleate, (phytosteryl/isostearyl/cetyl/stearyl/behenyl) dimer-dilinoleate, dimer-dilinoleyl dimer-dilinoleate, dimer-dilinoleyl diisostearate, dimer-dilinoleyl-hydrogenated rosin condensates, hydrogenated castor oil dimer-dilinoleate, and hydroxyalkyl dimer-dilinoleyl ethers; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (paltamide MEA), palmitic acid diethanolamide (paltamide DEA), and coconut oil fatty acid methylethanolamide (cocamidemethyl MEA); silicones such as dimethicone (dimethylpolysiloxanes), dimethicone having a high degree of polymerization (dimethyl polysiloxanes having a high degree of polymerization), cyclomethicone (cyclic dimethylsiloxane, decamethylcyclopentasiloxane), phenyl trimethicone, diphenyl dimethicone, phenyl dimethicone, stearoxypropyldimethylamine, a (aminoethylaminopropyl methicone/dimethicone) copolymer, dimethiconol, a dimethiconol crosspolymer, a silicone resin, a silicone rubber, amino-modified silicones such as aminopropyl dimethicone and amodimethicone, cation-modified silicones, polyether-modified silicones such as dimethicone copolyols, polyglycerol-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified and polyether-modified silicones, amino-modified and polyether-modified silicones, alkyl-modified and polyether-modified silicones, and polysiloxane-oxyalkylene copolymers; and fluorine-based oil agents such as perfluorodecane, perfluorooctane, and perfluoropolyethers.

Preferable examples of the moisturizers and the touch improvers include polyols such as glycerol, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerol, polyglycerols, diethylene glycol, polyethylene glycols, dipropylene glycol, polypropylene glycols, and an ethylene glycol-propylene glycol copolymer and polymers of these polyols; glycol alkyl ethers such as diethylene glycol monoethyl ether (ethoxy diglycol), ethylene glycol monoethyl ether, ethylene glycol monobutyl ether, and diethylene glycol dibutyl ether; water soluble esters such as polyglyceryl-10 (eicosanedioate/tetradecanedioate) and polyglyceryl-10 tetradecanedioates; sugar alcohols such as sorbitol, xylitol, erythritol, mannitol, and maltitol; saccharides such as glucose, fructose, galactose, mannose, threose, xylose, arabinose, fucose, ribose, deoxyribose, maltose, trehalose, lactose, raffinose, gluconic acid, glucuronic acid, cyclodextrins (α-cyclodextrin, β-cyclodextrin, γ-cyclodextrin, and modified cyclodextrins such as maltosylated cyclodextrin and hydroxyalkylated cyclodextrins), β-glucan, chitin, chitosan, heparin and derivatives thereof, pectin, arabinogalactan, dextrin, dextran, glycogen, ethyl glucoside, and polymers or copolymers of glucosylethyl methacrylate, and derivatives of these saccharides; hyaluronic acid and sodium hyaluronate; sodium chondroitin sulfate; mucoitinsulfuric acid, charonin sulfate, keratosulfate, and dermatan sulfate; *Tremella fuciformis* extracts and *Tremella fuciformis* polysaccharides; fucoidan; tuberosa polysaccharides or natural polysaccharides; organic acids such as citric acid, tartaric acid, and lactic acid, and salts thereof; urea and derivatives thereof; 2-pyrrolidone-5-carboxylic acid and salts thereof such as a sodium salt; amino acids such as betaine (trimethylglycine), proline, hydroxyproline, alginine, lysine, serine, glycine, alanine, phenylalanine, tyrosine, β-alanine, threonine, glutamic acid, glutamine, asparagine, aspartic acid, cysteine, cysteine, methionine, leucine, isoleucine, valine, tryptophan, histidine, and taurine, and salts of these amino acids; protein peptides such as collagen, fish-derived collagen, atelocollagen, gelatin, elastin, collagen decomposed peptide, hydrolyzed collagen, hydroxypropylammonium chloride-hydrolyzed collagen, elastin decomposed peptide, keratin decomposed peptide, hydrolyzed keratin, conchiolin decomposed peptide, hydrolyzed conchiolin, silk protein decomposed peptide, hydrolyzed silk, lauroyl-hydrolyzed silk sodium, soybean protein decomposed peptide, wheat protein decomposed peptide, hydrolyzed wheat protein, casein decomposed peptide, and acylated peptide, and derivatives of these protein peptides; acylated peptides such as palmitoyl oligopeptide, palmitoyl pentapeptide, and palmitoyl tetrapeptide; silylated peptides; a culture solution for lactic acid bacterium, yeast extract, eggshell membrane protein, cow submaxillary gland mucin, hypotaurine, sesame lignan glycoside, glutathione, albumin, and milk serum; choline chloride and phosphorylcholine; animal/plant extracted components such as placenta extract, elastin, collagen, aloe extract, *hamamelis* water, sponge cucumber water, *chamomilla* extract, licorice extract, comfrey extract, silk extract, chestnut rose extract, yarrow extract, *eucalyptus* extract, and melilot extract, ceramides such as natural ceramide (type 1, 2, 3, 4, 5, 6), hydroxyceramide, pseudo-ceramide, sphingoglycolipid, and extracts containing ceramide and ceramide saccharide.

Preferable examples of the surfactants include anionic surfactants, nonionic surfactants, cationic surfactants, amphoteric surfactants, and polymer surfactants. Preferable examples of the surfactants include the following surfactants. Preferable examples of the anionic surfactants include salts of fatty acids such as potassium laurate and potassium myristate; alkyl sulfates such as sodium lauryl sulfate, triethanolamine lauryl sulfate, and ammonium lauryl sulfate; polyoxyethylene alkyl sulfates such as sodium laureth sulfate and triethanolamine laureth sulfate; salts of acyl-N-methylamino acids such as sodium cocoylmethyl taurate, potassium cocoylmethyl taurate, sodium lauroylmethyl taurate, sodium myristoylmethyl taurate, sodium lauroylmethyl alaninate, sodium lauroyl sarcosinate, triethanolamine lauroyl sarcosinate, and sodium methylalanine lauroyl glutamate; salts of acylamino acids such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroylmonoethanolamide succinate; fatty acid alkanolamide ether carboxylates; acyl lactates; polyoxyethylene aliphatic amine sulfates; fatty acid alkanolamide sulfates; fatty acid glyceride sulfates such as glycerol hydrogenated coconut oil fatty acid sulfate sodium salt; alkylbenzene polyoxyethylene sulfates; olefin sulfonates such as sodium α-olefin sulfonate; alkyl sulfosuccinates such as disodium lauryl sulfosuccinate and sodium dioctylsulfosuccinate; alkyl ether sulfosuccinates such as disodium laureth sulfosuccinate, sodium monolauroyl monoethanolamide polyoxyethylene sulfosuccinates, and sodium lauryl polypropylene glycol sulfosuccinates; alkyl benzene sulfonates such as sodium tetradecylbenzenesulfonate and triethanolamine tetradecylbenzenesulfonate; alkylnaphthalenesulfonates; alkanesulfonates; methyl ester salts of α-sulfo fatty acids; acylisethionic acid salts; alkyl glycidyl ether sulfonates; alkyl sulfo acetates; alkyl ether phosphates such as sodium laureth phosphate, sodium dilaureth phosphate, sodium trilaureth phosphate, and sodium monooleth phosphate; alkyl phosphates such as potassium lauryl phosphate; sodium caseinate; alkyl aryl ether phosphates; fatty acid amide ether phosphates; phospholipids such as phosphatidylglycerol, phosphatidylinositol, and phosphatidic acid; silicone-based anion surfactants such as carboxylic acid-modified silicone, phosphoric acid-modified silicone, and sulfuric acid-modified silicone. Preferable examples of the nonionic surfactants include polyoxyethylene alkyl ethers having various numbers of added molecules of polyoxyethylene such as laureth (polyoxyethylene lauryl ether) groups, ceteth (polyoxyethylene cetyl ether) groups, steareth (polyoxyethylene stearyl ether) groups, beheneth (polyoxyethylene behenyl ether) groups, isosteareth (polyoxyethylene isostearyl ether) groups, and octyldodeceth (polyoxyethylene octyldodecyl ether) groups; polyoxyethylene alkyl phenyl ethers; derivatives of castor oils and hydrogenated castor oils such as polyoxyethylene hydrogenated castor oils, polyoxyethylene castor oils, polyoxyethylene hydrogenated castor oil monoisostearates, polyoxyethylene hydrogenated castor oil triisostearates, polyoxyethylene hydrogenated castor oil monopyroglutamate-monoisostearate-diesters, and polyoxyethylene hydrogenated castor oil maleates; polyoxyethylene phytosterols; polyoxyethylene cholesterols; polyoxyethylene cholestanols; polyoxyethylene lanolins; polyoxyethylene reduced lanolins; polyoxyethylene-polyoxypropylene alkyl ethers such as polyoxyethylene-polyoxypropylene cetyl ethers, polyoxyethylene-polyoxypropylene 2-decyltetradecyl ethers, polyoxyethylene-polyoxypropylene monobutyl ethers, polyoxyethylene-polyoxypropylene hydrogenated lanolins, and polyoxyethylene-polyoxypropylene glycerol ethers, polyoxyethylene-polyoxypropylene glycols; (poly) glycerol polyoxypropylene glycols such as PPG-9 diglyceryl; glycerol fatty acid partial esters such as glyceryl stearate, glyceryl isostearate, glyceryl palmitate, glyceryl myristate, glyceryl oleate, glycerol coconut oil fatty acid ester, glycerol mono cottonseed oil fatty acid ester, glyceryl monoerucate, glyceryl sesquioleate, glyceryl ester of α,α'-oleic acid-pyroglutamic acid, and glyceryl monostearate malic acid; polyglycerol fatty acid esters such as polyglyceryl-2,3,4,5,6,8, or 10 stearates, polyglyceryl-6 or 10 di stearates, polyglyceryl-2 tri stearates, polyglyceryl-10 decastearates, polyglyceryl-2,3,4,5,6,8, or 10 isostearates, polyglyceryl-2 diisostearates (diglyceryl diisostearate), polyglyceryl-3 diisostearates, polyglyceryl-10 diisostearates, polyglyceryl-2 triisostearates, polyglyceryl-2 tetraisostearates, polyglyceryl-10 decaisostearates, polyglyceryl-2,3,4,5,6,8, or 10 oleates, polyglyceryl-6 dioleates, polyglyceryl-2 trioleates, and polyglyceryl-10 decaoleates; ethylene glycol mono fatty acid esters such as ethylene glycol monostearate; propylene glycol mono fatty acid esters such as propylene glycol monostearate; pentaerythritol fatty acid partial ester; sorbitol fatty acid partial ester; maltitol fatty acid partial ester; maltitol ether; sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; saccharide derivative partial esters such as sucrose fatty acid ester, methylglucoside fatty acid ester, and trehalose undecylate; alkyl glucosides such as caprylyl glucoside; alkylpolyglucosides; lanolin alcohol; reduced lanolin; polyoxyethylene fatty acid mono- and di-esters such as polyoxyethylene distearates, polyethylene glycol diisostearates, polyoxyethylene monooleates, and polyoxyethylene dioleates; polyoxyethylene propylene glycol fatty acid esters; polyoxyethylene glycerol fatty acid esters such as polyoxyethylene monooleates such as polyoxyethylene glycerol monostearates, polyoxyethylene glycerol monoisostearates, and polyoxyethylene glycerol triisostearates; polyoxyethylene sorbitan fatty acid esters such as polyoxyethylene sorbitan monooleates, polyoxyethylene sorbitan monostearates, polyoxyethylene sorbitan monooleates, and polyoxyethylene sorbitan tetraoleates; polyoxyethylene sorbitol fatty acid esters such as polyoxyethylene sorbitol monolaurates, polyoxyethylene sorbitol monooleates, polyoxyethylene sorbitol pentaoleates, and polyoxyethylene sorbitol monostearates; polyoxyethylene methylglucoside fatty acid esters; polyoxyethylene alkyl ether fatty acid esters; polyoxyethylene animal and vegetable oils and fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropyleneethylenediamine condensates; nature-originated surfactants such as saponin and sophorolipid; polyoxyethylene fatty acid amides; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (paltamide MEA), palmitic acid diethanolamide (paltamide DEA), and coconut oil fatty acid methylethanolamide (cocamide methyl MEA); alkyldimethylamine oxides such as lauramine oxide, cocamine oxide, stearamine oxide, and behenamine oxide; alkylethoxydimethylamine oxides; polyoxyethylene alkyl mercaptans; polyether-modified silicones such as dimethicone copolyols; and silicone-based nonionic surfactants such as polysiloxane-oxyalkylene copolymers, polyglycerol-modified silicones, and saccharide-modified silicones. Preferable examples of the cationic surfactants include alkyltrimethylammonium chlorides such as behentrimonium chloride, steartrimonium chloride, cetrimonium chloride, and lauryltrimonium chloride; alkyltrimethylammonium bromides such as steartrimonium bromide; dialkyldimethylammonium chlorides such as disteardimonium chloride and dicocodimonium chloride; fatty acid amido amines such as stearamidopropyl dimethylamine and stearamidoethyl diethylamine, and salts thereof; alkyletheramines such as stearoxypropyl dimethylamine, and salts or quaternary salts thereof; fatty acid amide-type quaternary ammonium salts such as long-chain fatty acid (12 to 31) aminopropylethyldimethylammonium ethyl sulfate and lanolin fatty acid aminopropylethyldimethylammonium ethyl sulfate; polyoxyethylene alkylamines and salts or quaternary salts thereof; alkylamine salts; fatty acid amide guanidium salt; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone-based cationic surfactants such as amino-modified silicones such as aminopropyl dimethicone and amodimethicone, cation-modified silicones, cation-modified and polyether-modified silicones, and amino-modified and polyether-modified silicones. Preferable examples of the amphoteric surfactants include N-alkyl-N,N-dimethyl amino acid betaines such as lauryl betaine (lauryldimethyl aminoacetic acid betaine); fatty acid amide alkyl-N,N-dimethyl amino acid betaines such as cocamidopropyl betaine and lauramidopropyl betaine; imidazoline-type betaines such as sodium cocoamphoacetate and sodium lauroamphoacetate; alkylsulfo betaines such as alkyl dimethyl taurines; sulfuric acid-type betaines such as alkyl dimethyl amino ethanol sulfuric acid esters; phosphoric acid-type betaines such as alkyl dimethyl amino ethanol phosphoric acid esters; phospholipids such as sphingophospholipids such as phosphatidylcholine, phosphatidyl ethanolamine, phosphatidylserine, and sphingomyelin, lysolecithin, hydrogenated soybean phospholipid, partially hydrogenated soybean phospholipid, hydrogenated egg yolk phospholipid, partially hydrogenated egg yolk phospholipid, and lecithin hydroxide; and silicone-based amphoteric surfactants. Preferable examples of the polymer surfactants include polyvinyl alcohols, sodium alginate, starch derivatives, tragacanth gum, copolymers of alkyl acrylates or alkyl methacrylates, and various silicone-based surfactants.

Preferable examples of the polymers, the thickeners, and the gelators include guar gum, locust bean gum, quince seed, carrageenan, galactan, gum arabic, tara gum, tamarind, furcellaran, karaya gum, sunset *hibiscus*, cara gum, tragacanth gum, pectin, pectic acid and salts such as a sodium salt thereof, alginic acid and salts such as a sodium salt thereof, and mannan; starches of rice, corn, potato, and wheat; xanthan gum, dextran, succinoglucan, curdlan, hyaluronic acid and salts thereof, xanthan gum, pullulan, gellan gum, chitin, chitosan, agar, brown alga extract, chondroitin sulfate salt, casein, collagen, gelatin, and albumin; celluloses and derivatives thereof such as methyl cellulose, ethyl cellulose, hydroxyethyl cellulose, hydroxypropyl cellulose, hydroxypropylmethyl cellulose, carboxymethyl cellulose and salts such as a sodium salt thereof, methylhydroxypropyl cellulose, sodium cellulose sulfate, dialkyldimethyl ammonium sulfate cellulose, crystalline cellulose, and powdered cellulose; starch polymers such as soluble starch, carboxymethyl starch, methylhydroxypropyl starch, and methyl starch, starch derivatives such as starch hydroxypropyltrimonium chloride, and aluminum corn starch octenylsuccinate; alginic acid derivatives such as sodium alginate and propylene glycol alginate ester; polyvinylpyrrolidones (PVP), polyvinylalcohols (PVA), vinylpyrrolidone-vinylalcohol copolymers, and polyvinyl methyl ethers; polyethylene glycols, polypropylene glycols, and polyoxyethylene-polyoxypropylene copolymers; amphoteric methacrylate ester copolymers such as (methacryloyloxyethylcarboxybetaine/alkyl methacrylate) copolymers and (acrylates/stearyl acrylate/ethylamine oxide methacrylate) copolymers; (dimethicone/vinyldimethicone) cross polymers, (alkyl acrylate/diacetoneacrylamide) copolymers, and AMP-(alkyl acrylate/diacetoneacrylamide) copolymers; polyvinyl acetate partially saponified products and maleic acid polymers; vinylpyrrolidone-dialkylaminoalkyl methacrylate copolymers; acrylic resin alkanolamines; polyesters and water-dispersible polyesters; polyacrylamides; copolymers of polyacrylate esters such as ethyl polyacrylates, carboxyvinyl polymers, polyacrylic acid and salts such as a sodium salt thereof, and copolymers of acrylate esters-methacrylate esters; copolymers of alkyl acrylates-alkyl methacrylates; cationized celluloses such as polyquaternium-10, diallyldimethylammonium chloride-acrylamide copolymers such as polyquaternium-7, acrylic acid-diallyldimethylammonium chloride copolymers such as polyquaternium-22, acrylic acid-diallyldimethylammonium chloride-acrylamide copolymers such as polyquaternium-39, copolymers of acrylate esters-cationized methacrylate esters, copolymers of acrylamides-cationized methacrylamides, acrylic acid-methyl acrylate-methacrylamidepropyltrimethylammonium chloride copolymers such as polyquaternium-47, and methacryloyl chloride choline ester polymers; cationized polysaccharides such as cationized oligosaccharides, cationized dextran, and guar hydroxypropyltrimonium chloride; polyethyleneimines; cation polymers; polymers of 2-methacryloyloxyethyl phosphorylcholine such as polyquaternium-51 and copolymers thereof with a butyl methacrylate-copolymer; polymer emulsions such as an acrylic resin emulsion, an ethyl polyacrylate emulsion, a polyacrylalkyl ester emulsion, a polyvinyl acetate resin emulsion, natural rubber latex, and synthetic latex; nitrocelluloses; polyurethanes and various copolymers; various silicones; various silicone-based copolymers such as an acryl-silicone graft copolymer; various fluorine-based polymers; 12-hydroxystearic acid and salts thereof; dextrin fatty acid esters such as dextrin palmitate and dextrin myristate; silicic anhydride and fumed silica (ultrafine particle silicic anhydride), magnesium aluminum silicate and magnesium sodium silicate, metal soaps, dialkylphosphoric acid metal salts, bentonite, hectorite, organic modified clay minerals, saccharose fatty acid esters, and fructo-oligosaccharide fatty acid esters. Among the above examples, celluloses and derivatives thereof, alginic acid and salts thereof, polyvinyl alcohols, hyaluronic acid and salts thereof, and collagen are preferable.

Preferable examples of the solvents and the propellants include lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyl diol; glycol ethers such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol; benzyloxyethanol; propylene carbonate; dialkyl carbonates; acetone; ethyl acetate; N-methylpyrrolidone; toluene; and propellants such as fluorocarbons, Freon gas for the next generation, LPG, dimethyl ether, and carbon dioxide.

Preferable examples of the antioxidants include tocopherol derivatives such as tocopherol (vitamin E) and tocopherol acetate; BHT and BHA; gallic acid derivatives such as propyl gallate; vitamin C (ascorbic acid) and/or derivative thereof; erythorbic acid and derivatives thereof; sulfites such as sodium sulfite; hydrogensulfites such as sodium hydrogensulfite; thiosulfates such as sodium thiosulfate; metabisulfites; thiotaurine and hypotaurine; thioglycerol, thiourea, thioglycolic acid, and cysteine hydrochloride.

Preferable examples of the reducing agents include thioglycolic acid, cysteine, and cysteamine.

Preferable examples of the oxidizing agents include hydrogen peroxide water, ammonium persulfate, sodium bromate, and percarbonic acid.

Preferable examples of the preservative agents, the antimicrobe agents, and the bactericides include hydroxybenzoic acid and salts thereof or esters thereof such as methylparaben, ethylparaben, propylparaben, and butylparaben; salicylic acid; sodium benzoate; phenoxy ethanol; 1,2-diols such as 1,2-pentanediol and 1,2-hexanediol; isothiazolinone derivatives such as methyl-chloro-isothiazolinone and methyl-isothiazolinone; imidazolinium urea; dehydroacetic acid and salts thereof; phenols; halogenated bisphenols such as triclosan; acid amides and quaternary ammonium salts; trichlorocarbanilide, zinc pyrithione, benzalkonium chloride, benzethonium chloride, sorbic acid, chlorhexidine, chlorhexidine glucanate, halocarban, hexachlorophene, and hinokitiol; phenols other than the above phenols such as phenol, isopropylphenol, cresol, thymol, p-chlorophenol, phenylphenol, and sodium phenylphenate; phenylethyl alcohol, photosensitive elements, antibacterial zeolite, and silver ion.

Preferable examples of the chelating agents include: edetates (ethylenediaminetetraacetates) such as EDTA, EDTA2Na, EDTA3Na, and EDTA4Na; hydroxyethylethylenediaminetriacetates such as HEDTA3Na; pentetates (diethylenetriaminepentaacetates); phytic acid, phosphonic acids such as etidronic acid, and salts such as a sodium salt thereof; sodium oxalate; polyamino acids such as polyaspartic acids and polyglutamic acids; sodium polyphosphates, sodium metaphosphate, and phosphoric acid; sodium citrate, citric acid, alanine, dihydroxyethylglycine, gluconic acid, ascorbic acid, succinic acid, and tartaric acid.

Preferable examples of the pH adjusters, the acids, and the alkalis include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propandiol, 2-amino-2-hydroxymethyl-1,3-propanediol, arginine, sodium hydroxide, potassium hydroxide, ammonia water, guanidine carbonate, and ammonium carbonate.

Preferable examples of the powder include inorganic powder having various sizes and shapes such as mica, talc, kaolin, sericite, montmorillonite, kaolinite, isinglass, white mica, phlogopite, synthetic isinglass, biotite, vermiculite, magnesium carbonate, calcium carbonate, aluminum silicate, barium silicate, calcium silicate, magnesium silicate, strontium silicate, a metal salt of tungstic acid, magnesium, zeolite, barium sulfate, baked calcium sulfate, calcium phosphate, fluoroapatite, hydroxyapatite, ceramic powder, bentonite, smectite, clay, mud, metal soaps (for example, zinc myristate, calcium palmitate, aluminum stearate), calcium carbonate, red iron oxide, yellow iron oxide, black iron oxide, ultramarine, Prussian blue, carbon black, titanium oxide, fine particle or ultrafine particle titanium oxide, zinc oxide, fine particle or ultrafine particle zinc oxide, alumina, silica, fumed silica (ultrafine particle silicic anhydride), mica titanium, fish scale foil, boron nitride, a photochromic pigment, synthetic fluorophlogopite, fine particle compound powder, gold, and aluminum; inorganic powder that is powder hydrophobized or hydrophilized by subjecting the above inorganic powder to treatment using various surface treating agents such as silicones such as hydrogen silicone and cyclic hydrogen silicone, other silanes, or titanium coupling agents; organic powder having various sizes and shapes such as starch, cellulose, nylon powder, polyethylene powder, poly(methyl methacrylate) powder, polystyrene powder, powder of a copolymer resin of styrene and acrylic acid, polyester powder, benzoguanamine resin powder, powder in which a polyethylene terephthalate and a poly(methyl methacrylate) are layered, powder in which a polyethylene terephthalate, aluminum, and epoxy are layered, urethane powder, silicone powder, and Teflon (registered trademark) powder, and surface treated powder; and organic-inorganic compound powder.

Preferable examples of the inorganic salts include sodium chloride-containing salts such as a salt, a crude salt, a rock salt, a sea salt, and a natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as monosodium dihydrogen phosphate, disodium hydrogen phosphate, and trisodium phosphate, potassium phosphates, calcium phosphates, and magnesium phosphates.

Preferable examples of the ultraviolet absorbers include benzoic acid-based ultraviolet absorbers such as p-aminobenzoic acid, p-aminobenzoic acid monoglycerol ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid methyl ester; anthranilic acid-based ultraviolet absorbers such as homomenthyl-N-acetylanthranilate; salicylic acid-based ultraviolet absorbers such as salicylic acid and sodium salt thereof, amyl salicylate, menthyl salicylate, homomenthyl salicylate, octyl salicylate, phenyl salicylate, benzyl salicylate, and p-isopropanolphenyl salicylate; cinnamic acid-based ultraviolet absorbers such as octyl cinnamate, ethyl 4-isopropyl-cinnamate, methyl 2,5-diisopropyl-cinnamate, ethyl 2,4-diisopropy-cinnamate, methyl 2,4-diisopropyl-cinnamate, propyl p-methoxycinnamate, isopropyl p-methoxycinnamate, isoamyl p-methoxycinnamate, 2-ethylhexyl p-methoxycinnamate (octyl p-methoxycinnamate), 2-ethoxyethyl p-methoxycinnamate (cinoxate), cyclohexyl p-methoxycinnamate, ethyl α-cyano-β-phenylcinnamate, 2-ethylhexyl α-cyano-β-phenylcinnamate (octocrylene), glyceryl mono-2-ethylhexanoyl-di-p-methoxycinnamate, and ferulic acid and derivatives thereof; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone 5-sulfonate, 4-phenylbenzophenone, 2-ethylhexyl-4'-phenyl-benzophenone 2-carboxylate, 2-hydroxy-4-n-octoxybenzophenone, and 4-hydroxy-3-carboxybenzophenon; 3-(4'-methylbenzylidene)-d,l-camphor; 3-benzylidene-d,l-camphor; 2-phenyl-5-methylbenzoxazole; 2,2'-hydroxy-5-methylphenyl-benzotriazole; 2-(2'-hydroxy-5'-t-octylphenyl)benzotriazole; 2-(2'-hydroxy-5'-methylphenyl)benzotriazole; dibenzalazine; dianisoylmethane; 5-(3,3-dimethyl-2-norbornylidene)-3-pentan-2-one; dibenzoylmethane derivatives such as 4-t-butylmethoxy-dibenzoylmethane; octyltriazone; urocanic acid derivatives such as urocanic acid and ethyl urocanate; 2-(2'-hydroxy-5'-methylphenyl)benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl anthranilate, rutin and derivatives thereof, and orizanol and derivatives thereof.

Preferable examples of the whitening agents include hydroquinone glucosides such as arbutin and α-arbutin, and esters thereof; ascorbic acid derivatives such as ascorbic acid, ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbic acid alkyl ethers such as ascorbic acid ethyl ether, ascorbic acid glucoside such as ascorbic acid-2-glucoside and fatty acid ester thereof, ascorbic acid sulfate ester, and ascorbyl tocopheryl phosphate; kojic acid, ellagic acid, tranexamic acid and derivatives thereof, ferulic acid and derivatives thereof, placenta extract, glutathione, orizanol, butyl resorcinol, oil-soluble *chamomilla* extract, oil-soluble licorice extract, *Tamarix chinensis* extract, and *Saxifraga sarementosa* extract.

Preferable examples of the vitamin groups and derivatives thereof include the vitamin A group such as retinol, retinol acetate, and retinol palmitate; the vitamin B group such as thiamine hydrochloride salt, thiamine sulfate salt, riboflavin, riboflavin acetate, pyridoxine hydrochloride, pyridoxine dioctarioate, pyridoxine dipalmitate, flavin adenine dinucleotide, cyanocobalamin, folic acids, nicotinic acid group such as nicotinic acid amide and benzyl nicotinate, and cholines; the vitamin C group such as ascorbic acid and salts such as a sodium salt thereof; the vitamin D; the vitamin E group such as α,β,γ,δ-tocopherol; other vitamins such as pantothenic acid and biotin; ascorbic acid derivatives such as ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbyl stearate, ascorbyl palmitate, and ascorbyl dipalmitate, ascorbic acid alkyl ethers such as ascorbic acid ethyl ether, ascorbic acid glucoside such as ascorbic acid-2-glucoside and fatty acid ester thereof, and ascorbyl tocopheryl phosphate; vitamin derivatives such as tocopherol derivatives such as tocopherol nicotinate, tocopherol acetate, tocopherol linoleate, tocopherol ferulate, and tocopherol phosphate, tocotrienol, and various vitamin derivatives.

Preferable examples of the agents for hair growth, the blood circulation accelerators, and the stimulants include: plant extracts/tinctures such as *Swertia japonica* extract, *capsicum* tincture, *Zingiber officinale* ROSC tincture, *Zingiber officinale* ROSC extract, and cantharides tincture; capsaicin, nonylic acid vanillylamide, zingerone, ichthammol, tannic acid, borneol, cyclandelate, cinnarizine, tolazoline, acetylcholine, verapamil, cepharanthine, γ-oryzanol, vitamin E and derivatives thereof such as tocopherol nicotinate and tocopherol acetate, γ-oryzanol, nicotinic acid and derivertive of nicotinic acid such as nicotinic amide, benzyl nicotinate, inositol hexanicotinate, and nicotinic alcohol; allantoin, a photosensitive element 301, a photosensitive element 401, capronium chloride, pentadecanoic acid monoglyceride, flavanonol derivatives, stigmasterol or stigmastanol and glucoside thereof, and minoxidil.

Preferable examples of the hormones include estradiol, estrone, ethinylestradiol, cortisone, hydrocortisone, and prednisone.

Preferable examples of other medical agents such as the anti-wrinkle agents, the anti-aging agents, the tightening agents, the cold sensing agents, the warm sensing agents, the wound healing promoters, the irritation mitigators, the analgesics, and the cell activators include retinols, retinoic acids, and tocopheryl retinoate; lactic acid, glycolic acid, gluconic acid, fruit acids, salicylic acid, and glucoside and ester compounds thereof; α- or β-hydroxy acids and derivatives thereof such as hydroxycapric acid, long-chain α-hydroxy fatty acids, and long-chain α-hydroxy fatty acid cholesteryl esters; γ-amino butyric acid and γ-amino-β-hydroxy butyric acid; carnitine; carnosine; creatine; ceramides and sphingosines; caffeine and xanthin, and derivatives thereof; antioxidants/active oxygen eliminating agents such as coenzyme Q10, carotene, lycopene, astaxanthin, lutein, α-lipoic acid, platinum nanocolloid, and fullerenes; catechins; flavones such as quercetin; isoflavones; gallic acid and ester saccharide derivatives thereof; polyphenols such as tannin, sesamin, protoanthocyanidin, chlorogenic acid, and apple polyphenols; rutin and derivatives thereof such as glucoside thereof; hesperidin and derivatives thereof such as glucoside thereof; lignan glucoside; substances related to licorice extract such as glabridin, glabrene, liquiritin, and isoliquiritin; lactoferrin; shogaol and gingerol; perfumery materials such as menthol and cedrol, and derivatives thereof; capsaicin and vanillin, and derivatives thereof; insect repellents such as diethyltoluamide; and complexes of physiologically active substances and cyclodextrins.

Preferable examples of the plant/animal/microbe extracts include extracts such as iris extract, *Angelica keiskei* extract, *Thujopsis dolabrata* extract, asparagus extract, avocado extract, *Hydrangea Serrata* leaf extract, almond extract, *Althaea officinalis* extract, *Arnica montana* extract, aloe extract, apricot extract, apricot kernel extract, *Gingko biloba* extract, *Artemisia capillaris* flower extract, fennel fruit extract, turmeric root extract, oolong tea extract, *Arctostaphylos uva-ursi* extract, *Rosa multiflora* extract, *Echinacea angustifolia* leaf extract, *Isodon japonicus* extract, *Scutellaria baicalensis* root extract, *Phellodendron amurense* bark extract, *Coptis rhizome* extract, *Hordeum vulgare* seed extract, *Panax ginseng* extract, *Hypericum erectum* extract, *Lamium album* extract, *Ononis spinosa* extract, *Nasturtium officinale* extract, orange extract, sea water dried products, sea weed extract, Japanese persimmon leaf extract, *Pyracantha fortuneana* extract, hydrolyzed elastin, hydrolyzed wheat flour, hydrolyzed silk, *Pueraria lobata* root extract, Chamomile extract, oil-soluble Chamomile extract, carrot extract, *Artemisia capillaris* flower extract, wild oat extract, *Hibiscus sabdariffa* extract, licorice extract, oil-soluble licorice extract, kiwi fruit extract, Kiou extract, *Auricularia auricula-judae* extract, cinchona bark extract, cucumber extract, *Paulownia tomentosa* leaf extract, guanosine, guava extract, *sophora* root extract, *Gardenia florida* extract, *Sasa veitchii* extract, *Sophora angustifolia* extract, walnut extract, Japanese chestnut extract, grapefruit extract, *clematis* extract, black rice extract, a brown sugar extracted substance, black vinegar, *chlorella* extract, mulberry extract, *Gentiana lutea* extract, *Geranium nepalense* herb extract, black tea extract, yeast extract, *Magnolia officinalis* bark extract, coffee extract, burdock extract, rice extract, fermented rice extract, fermented rice bran extract, rice germ oil, comfrey extract, collagen, *Vaccinium vitis-idaea* extract, asiasarum root extract, bupleurum root extract, umbilical extract, saffron extract, *Salvia sclarea* extract, *Saponaria officinalis* extract, *Sasa* bamboo grass extract, *Crataegus cuneata* fruit extract, *Bombyx mori* excrementum extract, *Zanthoxylum piperitum* extract, shiitake mushroom extract, *Rehmannia glutinosa* root extract, *Lithospermum erythrorhizone* root extract, *Perilla ocymoides* extract, *Tilia japonica* flower extract, *Spiraea ulmaria* flower extract, *Hymenaea coubaril* extract, *Paeonia albiflora* extract, *Zingiber officinale* extract, *Acorus calamus* root extract, *Betula alba* extract, *Tremella fusciformis* extract, *Equisetum arvense* extract, *Stevia rebaudiana* extract, *Stevia rebaudiana* fermentation product, *Tamarix chinensis* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, mulberry bark extract, *Rheum officinale* extract, soybean extract, *Ziziphus jujuba* extract, thyme extract, dandelion extract, lichenes extract, tea extract, *Eugenia caryophyllus* flower extract, *Imperata cylindrica* extract, *Aurantii nobilis pericarpium* extract, tea tree oil, *Rubus suavissimus* leaf extract, red pepper extract, *Angelica Acutiloba* root extract, *Calendula officinalis* extract, *Persicae semen* extract, *Citrus aurantium* peel extract, *Houttuynia cordata* extract, tomato extract, natto extract, *ginseng* extract, garlic extract, *Rosa canina* fruit extract, *hibiscus* extract, *Ophiopogon tuber* extract, *Nelumbo nucifera* extract, parsley extract, birch extract, honey, *Hamamelis virginiana* extract, *Parietaria officinalis* extract, *Isodonis japonicus* extract, bisabolol, *Chamaecyparis obtusa* extract, *Lactobacillus bifidus* extract, *Eriobotrya japonica* extract, *Tussilago Farfara* extract, *Petasites japonicus* extract, *Poria cocos* extract, butcher's broom extract, grape extract, grape seed extract, propolis, *Luffa cylindrica* extract, safflower flower extract, peppermint extract, *Tilia Platyphyllos* flower extract, *Paeonia suffruticosa* root extract, hops extract, *Rosa rugosa* flower extract, pine cone extract, *Aesculus hippocastanum* extract, *Lysichiton camtschatcense Schott* extract, *Sapindus mukurossi* peel extract, *Melissa officinalis* extract, *Cladosiphon okamuranus* extract, peach extract, *Centaurea cyanus* flower extract, *Eucalyptus globulus* leaf extract, *Saxifraga sarementosa* extract, *Citrus junos* extract, lily extract, *Coix lacryma-jobi* var. *ma-yuen* seed extract, *Artemisia princeps* extract, lavender extract, green tea extract, eggshell membrane extract, apple extract, rooibos tea extract, lychee extract, lettuce extract, lemon extract, *Forsythia suspensa* extract, *Astragalus sinicus* extract, rose extract, rosemary extract, *Anthemis nobilis* flower extract, royal jelly extract, and *Sanguisorba officinalis* extract.

Examples of the antipruritic agents include diphenhydramine hydrochloride, chlorpheniramine maleate, camphor, and a substance-P inhibitor.

Examples of the corneum releasing/dissolving agents include salicylic acid, sulfur, resorcin, selenium sulfide, and pyridoxine.

Examples of the antiperspirants include chlorhydroxyaluminum, aluminum chloride, zinc oxide, and zinc p-phenolsulfonate.

Examples of the refrigerants include menthol and methyl salicylate.

Examples of the astringent agents include citric acid, tartaric acid, lactic acid, aluminum potassium sulfate, and tannic acid.

Examples of the enzymes include superoxide dismutase, catalase, lysozyme chloride, lipase, papain, pancreatin, and protease.

Preferable examples of the nucleic acids include ribonucleic acids and salts thereof, deoxyribo nucleic acids and salts thereof, and adenosine triphosphate disodium salt.

Preferred examples of the perfume include synthetic perfumes, natural perfumes, and various compound perfumes such as acetyl cedrene, amylcinnamaldehyde, allyl amyl glycolate, β-ionone, Iso E Super, isobutyl quinoline, iris oil, irone, indole, ylang oil, undecanal, undecenal, γ-undecalactone, estragole, eugenol, oakmoss, Opopanax resinoid, orange oil, eugenol, aurantiol, galaxolide, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-tert-butylcyclohexyl acetate, vetiveryl acetate, benzyl acetate, linalyl acetate, isopentyl salicylate, benzyl salicylate, sandal wood oil, santalol, cyclamen aldehyde, cyclopentadecanolide, methyl dihydrojasmonate, dihydromyrcenol, jasmine absolute, jasmine lactone, cis-jasmone, citral, citronellol, citronellal, cinnamon bark oil, 1,8-cineole, cinnamaldehyde, *Styrax* resinoid, cedar wood oil, cedrene, cedrol, celery seed oil, thyme oil, damascone, damascenone, thymol, tuberose absolute, decanal, decalactone, terpineol, γ-terpinene, triplal, nerol, nonanal, 2,6-nonadienol, nonalactone, patchouli alcohol, Vanilla Absolute, vanillin, basil oil, patchouli oil, hydroxycitronellal, α-pinene, piperitone, phenethyl alcohol, phenylacetoaldehyde, petitgrain oil, hexylcinnamaldehyde, cis-3-hexenol, Peruvian balsam, vetiver oil, vetiverol, peppermint oil, pepper oil, heliotropin, Bergamot oil, benzyl benzoate, borneol, myrrh resinoid, musk ketone, methylnonylacetoaldehyde, γ-methylionone, menthol, L-menthol, L-menthone, *eucalyptus* oil, β-ionone, lime oil, lavender oil, d-limonene, linalool, lyral, lilial, lemon oil, rose absolute, rose oxide, rose oil, rosemary oil, and various refined oils.

Preferable examples of the coloring matters, the colorants, the dyes, and the pigments include legal coloring matters such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow 201, Yellow 202-1, Yellow 202-2, Yellow 203, Yellow 204, Yellow 205, Yellow 4, Yellow 401, Yellow 402, Yellow 403-1, Yellow 404, Yellow 405, Yellow 406, Yellow 407, and Yellow 5; other acid dyes such as Acid Red 14; basic dyes such as Arianor Sienna Brown, Arianor Madder Red, Arianor Steel Blue, and Arianor Straw Yellow; nitro dyes such as HC Yellow 2, HC Yellow 5, HC Red 3, 4-hydroxypropylamino-3-nitrophenol, N,N'-bis(2-hydroxyethyl)-2-nitro-p-phenylenediamine, HC Blue 2, and Basic Blue 26; disperse dyes; inorganic white pigments such as titanium dioxide and zinc oxide; inorganic red-based pigments such as iron oxide (red iron oxide) and iron titanate; inorganic brown-based pigments such as γ-ferric oxide; inorganic yellow-based pigments such as yellow iron oxide and ocher; inorganic black-based pigments such as black iron oxide and black lower-order titanium oxide; inorganic violet-based pigments such as mango violet and cobalt violet; inorganic green-based pigments such as chromium oxide, chromium hydroxide, and cobalt titanate; inorganic blue-based pigments such as ultramarine blue and Prussian blue; pearl pigments such as titanium oxide-coated mica, titanium oxide-coated bismuth oxychloride, titanium oxide-coated talc, colored titanium oxide-coated mica, bismuth oxychloride, and fish scale foil; metal powder pigments such as aluminum powder, copper powder, and gold; surface-treated inorganic and metal powder pigments; organic pigments such as a zirconium lake, a barium lake, and an aluminum lake; surface-treated organic pigments; natural coloring matters and dyes such as anthraquinones such as astaxanthin and alizarin, anthocyanidin, β-carotene, catenal, capsanthin, chalcone, carthamin, quercetin, crocin, chlorophyll, curcumin, cochineal, naphthoquinones such as shikonin, bixin, flavones, betacyanidine, henna, hemoglobin, lycopene, riboflavin, and rutin; oxidation dye intermediates and couplers such as p-phenylenediamine, toluene-2, 5-diamine, o-, m-, or p-aminophenol, m-phenylenediamine, 5-amino-2-methylphenol, resorcin, 1-naphthol, and 2,6-diaminopyridine, and salts thereof; naturally oxidized-type dyes such as indoline; and dihydroxyacetone.

Preferable examples of the antiphlogistic agents and the antiinflammatory agents include glycyrrhizic acid and derivatives thereof, glycyrrhetic acid derivatives, salicylic acid derivatives, hinokitiol; guaiazulene, allantoin, indomethacin, ketoprofen, ibuprofen, diclofenac, loxoprofen, celecoxib, infliximab, etanercept, zinc oxide, hydrocortisone acetate, prednisone, diphenhydramine hydrochloride, and chlorpheniramine maleate; and plant extracts such as peach leaf extract and *Artemisia princeps* leaf extract.

Preferable examples of the antiasthmatic agents, the antichronic obstructive pulmonary disease agents, the antiallergic agents, and the immunomodulators include aminophylline, theophyllines, steroids (fluticasone, beclomethasone, and the like), leukotriene antagonists, thromboxane inhibitors, intal, β-2 stimulants (formoterol, salmeterol, albuterol, tulobuterol, clenbuterol, epinephrine, and the like), tiotropium, ipratropium, dextromethorphan, dimemorfan, bromhexine, tranilast, ketotifen, azelastine, cetirizine, chlorpheniramine, mequitazine, tacrolimus, cyclosporine, sirolimus, methotrexate, cytokine regulating agents, interferon, omalizmab, and protein/antibody formulations.

Preferable examples of the anti-infectious disease agents and the antifungal agents include oseltamivir, zanamivir, and itraconazole.

In the cosmetic base material or medical base material of the present invention, there may be blended as additives other than the above additives, publicly known ingredients for cosmetics, medicines, and foods such as ingredients described in the Japanese Standards of Cosmetic Ingredients, the Japanese Cosmetic Ingredients Codex, the Japan Cosmetic Industry Association list of displayed names of ingredients, the INCI dictionary (the International Cosmetic Ingredient Dictionary and Handbook), the Japanese Standards of Quasi-drug Ingredients, the Japanese Pharmacopoeia, the Japanese Pharmaceutical Excipients, and the Japan's Specifications and Standards for Food Additives, and ingredients described in Patent Publications and Patent Unexamined Application Publications (including Japanese or each language Translation of PCT International Application Publications and Re-publications of PCT International Publications) of Japan and various other countries that are classified by the International Patent Classification into the classes A61K7 and A61K8, in a publicly known combination and in a publicly known blending ratio/blending amount.

Generally, as commercially available cosmetics, facial cleansers, body soaps, makeup removers, and the like are produced by adding, for example, surfactants and disinfectants as cleansing components, oily base materials such as polyhydric alcohols and fatty acid esters as emollient components, moisturizers, oily base materials, and thickeners as moisturizing components, and antiphlogistics as rough skin-ameliorating components, and by further adding preservative agents, stabilizers, and the like. A powder can be further added to adjust the viscosity.

Lotions, cosmetic fluids, and the like are produced by adding, for example, water and inorganic salts as base components, oily base materials such as polyhydric alcohols and fatty acid esters and plant extracts as moisturizing components, thickeners, antiphlogistics as rough skin-ameliorating components, and vitamins, skin-brightening agents, antioxidants, anti-wrinkle agents, anti-aging agents, tightening agents, or the like as functional components.

Creams are produced by adding, for example, water and gelators as base components, oily base materials such as polyhydric alcohols and fatty acid esters as emollient components, moisturizers, oily base materials, and thickeners as moisturizing components, emulsifiers, and antioxidizing agents or the like as functional components.

Eye care products and the like are produced by adding, for example, water as a base component, oily base materials such as silicone oils, vegetable oils, and fatty acid esters as emollient components, moisturizers such as polyhydric alcohols as moisturizing components, thickeners, emulsifiers, and antioxidizing agents or the like as functional components.

Base makeup products, lip rouge, and the like are produced by adding, for example, water and inorganic salts as base components, oily base materials such as silicone oils, fatty acid esters, polyhydric alcohols, and fatty acids as emollient components, oily base materials such as polyhydric alcohols, moisturizers as moisturizing components, and pigments.

Blusher, powdery foundations, and the like are produced by adding, for example, gelators and inorganic salts as base components, thickeners as an emollient component, pigments, essential oils, and powders.

Nail color removers and the like are produced by adding, for example, oily base materials such as esters as base components, oily base materials such as oils/fats as emollient components, and thickeners.

UV care performance can be provided to the cosmetics by adding hydrocarbons and waxes as antioxidizing agents, inorganic salts and powders as ultraviolet-scattering components, ultraviolet absorbers, and the like.

The sugar derivative gelator of the present invention, which acts as a gelator and a thickener in cosmetic products, can replace the gelators and/or the thickeners in these conventional, commercially available cosmetics. The sugar derivative gelator provides further safety and feeling in use than these conventional cosmetics.

Examples of the cosmetic products including the sugar derivative gelator of the present invention include basic care cosmetic products, makeup cosmetic products, body care cosmetic products, fragrance cosmetic products, and hair care cosmetic products. The cosmetics, however, are not limited to these examples.

The basic care products refer to facial cleansers, makeup removers, lotions, milk lotions, cosmetic fluids, facial creams, facial packs, eye cosmetics, and other facial skin care products.

Examples of the basic care products include facial cleansers such as bar soaps, foaming cleansers, powder cleansers, and sheet cleansers; makeup removers such as foaming makeup removers, cream-type makeup removers, milk-type makeup removers, lotion-type makeup removers, gel-type makeup removers, oil-type makeup removers, and mask-type makeup removers; lotions such as liposome lotions, softening lotions, astringent lotions, cleanser lotions, and multi-layered lotions; milk lotions such as emollient lotions, moisturizing lotions, milky lotions, nourishing lotions, nourishing milk lotions, skin moisturizers, moisturizing emulsions, massage lotions, and facial keratin smoothers; cosmetic fluids such as liposome lotions, moisturizing fluids, whitening fluids, and anti-UV fluids; creams such as emollient creams, enriched creams, nourishing creams, vanishing creams, moisturizing creams, night creams, massage creams, cream-type makeup removers, makeup creams, base creams, shaving creams, and facial keratin-softening creams; facial packs such as peel off-type facial packs, powder-type facial packs, wash off-type facial packs, oil-type facial packs, and mask-type makeup removers; eye cosmetics such as eye serums, eye gels, and eye creams; UV care products such as facial UV-protection emulsions, sun protection products, sun protectors, UV-care milk lotions, sunscreens, sunscreen creams, and suntan creams, gels such as moisturizing gels, facial peeling products, facial slimming products, and other basic cosmetics.

Examples of the makeup cosmetics include base makeup cosmetics and point makeup cosmetics.

The base makeup cosmetic products refer to basic makeup that is applied to complement point makeup, and refer to makeup base products, concealers, foundations, and face powders. Examples of the base makeup cosmetic products include makeup base products such as makeup bases, base creams, color-controlling bases, and UV protection bases; concealers such as powdery concealers, cream concealers, and liquid concealers; foundations such as powdery foundations, UV protection foundations, cream foundations, and UV protection cream foundations; face powders such as loose powders, pressed powders, face color products, and white face powders.

The point makeup cosmetic products refer to cosmetic products for coloring the skin to make the skin look beautiful, and examples of the point makeup cosmetic products include eye color products, eyeliners, mascaras, eyebrow cosmetics, blusher, lip color products, and nail color products.

Examples thereof include eye color products such as eye color powders, eye color pencils, and eye shadows; eyeliners such as eyeliner pencils and liquid eyeliners; eyelash liners such as volume-up eyelash liners, long lash eyelash liners, curling eyelash liners, and color eyelash liners; eyebrow cosmetics such as eyebrow pencils, eyebrow powders, and liquid eyebrows; blushers such as powder blusher and cream blusher; lip color products such as lip color products, lipsticks, lip rouge, lip glosses, and lip liners; and nail color products such as nail color products, manicures, nail-top coats, base coats, top coats, over-top coats, nail color removers, nail polish removers, nail color thinners, and nail treatments.

Examples of the body cosmetics products include body lotions, body creams, lip balms, hand creams, UV care products, depilatory products, foot care products, and anti-perspirants/deodorants.

Examples of the body cosmetics products include body lotions such as body lotions, body oils, and body mists; body creams such as body creams, body milk lotions, body gels, and body mousses; lip balms such as moisturizing lip balms, UV-care lip balms, and colored lip balms; hand creams such as hand creams and hand gels; UV care products for body such as UV-protection emulsions, sun protection products, sun protectors, UV-care milk lotions, sunscreens, sunscreen creams, and suntan creams; depilatory products such as depilatory creams, depilatory mousses, depilatory waxes, body hair bleaches, and body shaving creams; foot care products such as foot massage products, foot slimming products, foot peeling products, non-facial exfoliators including exfoliators for heel, and emollient products; anti-perspirants/deodorants such as deodorant lotions, deodorant powders, deodorant sprays, and deodorant sticks; and insect repellents such as insect repellent sprays.

Examples of the fragrance cosmetic products include perfumes, parfums, eau de parfums, eau de toilettes, eau de colognes, solid perfumes, powder fragrances, perfumed soaps, and bath oils.

Examples of the hair care cosmetic products include shampoos, hair rinses and conditioners, hair treatments and hair packs, hair styling products, hair sprays and hair glosses, hair growth promoters and pilatories, hair permanent products, and hair coloring products.

Examples of the hair care cosmetic products include shampoos such as oil shampoos, cream shampoos, conditioning shampoos, anti-dandruff shampoos, shampoos for colored hair, and 2-in-1 shampoos; hair rinses and conditioners such as hair rinses and conditioners, anti-dandruff/scalp-care hair rinses and conditioners, and control hair rinses and conditioners; hair treatments and packs such as damaged hair treatments and packs, damaged hair treatments and packs, anti-dandruff/scalp-care treatments and packs, and control treatments and packs; styling products such as hair foams, hair creams, hair wax, hair gels, hair water, hair lotions, hair oils, and hair liquids; hair sprays and hair glosses such as hair styling sprays, hair styling mists, and hair glosses, and hair growth promoters and pilatories such as hair growth promoters, pilatories, hair tonics, and hair essences; hair permanent products such as straight permanent treatment agents, waving permanent agents, permanent pre-treatments, and permanent after-treatments; and hair coloring products such as oxidative hair dyes, hair bleaches, hair coloring pre-treatments, hair coloring after-treatments, and hair manicures.

[Ionic Liquid]

The gelator of the present invention can form gels of not only the above hydrophobic organic solvent and hydrophilic organic solvent but also ionic liquid.

In other word, the present invention includes the above gelator that is a gelator for an ionic liquid and further includes a gel including the gelator and the ionic liquid.

As the ionic liquid, a liquid generally known as "ionic liquid" can be used. Examples of the ionic liquid include liquids composed of cations selected from the group consisting of imidazolium, pyridinium, piperidinium, pyrrolidinium, phosphonium, ammonium and sulfonium and anions selected from the group consisting of halogen, carboxylate, sulfate, sulfonate, thiocyanate, nitrate, aluminate, borate, phosphate, amide, antimonate, imide, and methide.

Examples of the cationic species include 1,3-dialkylimidazolium ions, 1,2,3-trialkylimidazolium ions, N-alkylpyridinium ions, N-alkylpyrrolidiniums, tetraalkylammonium ions, tetraalkylphosphonium ions, and trialkylsulfonium ions.

Examples of the anion species include tetrafluoroborate ($BF_4^-$) ion, hexafluorophosphate ($PF_6^-$) ion, trifluoromethanesulfonate ($CF_3SO_3^-$) ion, hexafluoroantimonate ($SbF_6^-$) ion, bis(trifluoromethylsulfonyl)imide ($(CF_3SO_2)_2N^-$) ion, bis(fluorosulfonyl)imide ($(FSO_2)_2N^-$) ion, tris(trifluoromethylsulfonyl)methide ($(CF_3SO_2)_3C^-$) ion, nitrate ($NO_3^-$) ion, trifluoromethylcarboxylate ($CF_3CO_2^-$) ion, carboxylate ($CH_3CO_2^-$) ion, and chloroaluminate ($Al_2Cl_7^-$) ion.

[Gel Electrolyte]

The gel of the present invention can be used as a gel electrolyte. The gel electrolyte is obtained by forming the gel of an electrolytic solution (liquid electrolyte) including an organic solvent or water and further by forming the gel of the ionic liquid. The gelator and the electrolytic solution to be used are not particularly limited and may be appropriately selected depending on use.

For example, in the case of the electrolytic solution including the organic solvent, an electrolyte salt is dissolved in at least one of aprotic organic solvents.

Examples of the aprotic organic solvents include glymes, alkene carbonates, alkyl carbonates, cyclic ethers, amides, nitriles, ketones and esters. Preferable example of these organic solvents include propylene carbonate, ethylene carbonate, diethyl carbonate, γ-butyrolactone, 1,2-dimethoxyethane, tetrahydrofuran, 2-methyltetrahydrofuran, dimethylsulfoxide, 1,3-dioxolane, formamide, dimethylformamide, 1,4-dioxane, acetonitrile, nitromethane, ethyl monoglyme, phosphoric triester, trimethoxymethane, dioxolane derivatives, sulfolane, 3-methyl-2-oxazolidinone, propylene carbonate derivatives, tetrahydrofuran derivatives, diethyl ether, and 1,3-propanesultone. These organic solvents may be used singly or in combination of two or more of them.

The electrolyte salt is composed of a cation metal and a counter anion. Examples of the cation metal include $Li^+$, $Na^+$, and $K^+$ and examples of the counter anion include $ClO_4^-$, $LiBF_4^-$, $PF_6^-$, $CF_3SO_3^-$, $CF_3CO_2^-$, $AsF_6^-$, $SbF_6^-$, $(CF_3SO_2)_2N^-$, $B_{10}Cl_{10}^{2-}$, $(1,2\text{-dimethoxyethane})_2ClO_4^-$, lower aliphatic carboxylic acid salts, $AlCl_4^-$, $Cl^-$, $Br^-$, $I^-$, chloroborane compounds, and tetraphenylboronic acid. Among them, the lithium salt is exemplified as a preferable electrolyte salt. These electrolyte salts may be used singly or in combination of two or more of them.

[Method for Producing Gelator]

The present invention also includes a method for producing the compound of Formula (1) or Formula (2) that is the above gelator of the present invention.

The method for producing the compound is a method characterized by comprising producing a compound of Formula (1) or Formula (2) by annelation reaction of a compound of a formula $R_1$—CHO (wherein $R_1$ is a linear or branched alkyl group having a carbon atom number of 9 to 20, a cyclic alkyl group having a carbon atom number of 13 to 20, or a linear or branched alkenyl group having a carbon atom number of 9 to 20) with glucose, mannose, galactose, or a derivative thereof in a single pot in the presence of triethyl orthoformate, DMF, and p-toluenesulfonic acid.

EXAMPLES

Hereinafter, Examples will be described in order to further clarify the characteristics of the present invention. The present invention, however, is not limited by Examples.

The reagents used as synthetic raw materials in Examples are shown below.

1-Octadecanol, 1-tetradecanol (special grade), 1-hexadecanol (primary grade), 1-dodecanal, ethyl α-D-glucopyranoside (for food analysis), methyl α-D-mannopyranoside (special grade), methyl α-D-galactopyranoside monohydrate, tetrabutylammonium bromide, and potassium carbonate were obtained from Wako Pure Chemical Industries, Ltd. and N-chlorosuccinimide, 2,2,6,6-tetramethylpiperidine-1-oxyl, methyl α-D-glucopyranoside, p-toluenesulfonic acid monohydrate, triethyl orthoformate, 1-undecanal, and methyl β-D-glucopyranoside 0.5 hydrate were obtained from Tokyo Chemical Industry Co., Ltd.

N,N-dimethylformamide (DMF) (for dehydration and organic synthesis) and dichloromethane (special grade) were obtained from Wako Pure Chemical Industries, Ltd. and hexane (special grade) was obtained from Kanto Chemical Co. These solvents were used as reaction solvents.

Triethylamine (special grade), sodium sulfate (special grade), sodium hydrogen carbonate (special grade), ethanol (special grade), acetonitrile (special grade), diethyl ether (special grade), sodium chloride (special grade), and toluene (special grade) were obtained from Wako Pure Chemical Industries, Ltd. and hexane (special grade), ethyl acetate (special grade), methanol (special grade), and chloroform (special grade) were obtained from Kanto Chemical Co. These compounds were used for treatment after reaction and for purification.

Pure water was used as water. Deuterochloroform (containing 0.03% of TMS (tetramethylsilane)) used for NMR measurement was obtained from Sigma-Aldrich Japan Co., Ltd.

Solvents and reagents used in the following gelation test and emulsion preparation are shown below.

Octane (special grade), cyclohexane (special grade), squalene (special grade), toluene (special grade), sodium dodecyl sulfate (for biochemistry), uranine (special grade), Rhodamine B (special grade), isopropyl myristate (special grade), olive oil (primary grade), ethanol (special grade), squalane (special grade), polyoxyethylene (20) sorbitan monolaurate (equivalent to Tween 20), L-ascorbic acid, glycine, L-ascorbic acid 2-phosphate trisodium were obtained from Wako Pure Chemical Industries, Ltd., dimethylsulfoxide (DMSO), 1-butyl-3-methylimidazolium tetrafluoroborate ([BuMeIm][$BF_4$], trimethylpropylammonium bis(trifluoromethanesulfonyl)imide ([TMPA][TFSI]), hexadecylpyridinium chloride monohydrate (CPC), hexadecyltrimethylammonium bromide (CTAB), sodium sulfosuccinate bis (2-ethylhexyl) (AOT), Span 80 (sorbitan monooleate), and D-(+)-glucosamine hydrochloride were obtained from Tokyo Chemical Industry Co., Ltd., chloroform (special grade), ethyl acetate (special grade), acetonitrile (special grade), ethylene glycol (special grade), methanol (special grade), 1-ethyl-3-methylimidazolium bis (trifluoromethylsulfonyl)imide ([EtMeIm][TFSI]), 1-butyl-3-methylimidazolium iodide ([BuMeIm][I]), 1-butyl-3-methylimidazolium hexafluorophosphate ([BuMeIm][$PF_6$]), 1-butyl-3-methylimidazolium triflate ([BuMeIm][$CF_3SO_3$]), 1-butylpyridinium bis(trifluoromethylsulfonyl)imide ([BuPy][TFSI]), and N-methyl-N-propylpyrrolidinium bis(trifluoromethanesulfonyl)imide ([P13][TF SI]) were obtained from Kanto Chemical Co., 1-butyl-3-methylimidazolium bis(trifluoromethylsulfonyl)imide ([BuMeIm][TFSI]) was obtained from Sigma-Aldrich Japan LLC, 1-hexyl-3-methylimidazolium bis(trifluoromethylsulfonyl)imide [HeMeIm][TFSI] was obtained from Merck KGaA, SH245 (decamethylcyclopentasiloxane) was obtained from Dow Corning Toray Co., Ltd., KF995 (decamethylcyclopentasiloxane) was obtained from Shin-Etsu Silicone Co., Ltd., jojoba oil was obtained from Ryohin Keikaku Co., Ltd., and Talc DN-SH, Titanium DN-SH (2), and Sericite DN-MC(2), DN-HAP(SH) were obtained from Dainippon Kasei Corporation. Pure water was used as water.

The apparatus and conditions used for various measurements, analysis, and polymerization are shown below.

(1) $^1$H-NMR Spectrum
  Apparatus: AVANCE 500, manufactured by Bruker-BioSpin Co., Ltd. JNM-ECS 400, manufactured by JEOL Ltd.
(2) Vortex mixer
  Apparatus: Voltex Genie 2, manufactured by Scientific Industries
(3) Confocal laser scanning microscope
  Apparatus: LSM 700, manufactured by Carl Zeiss Co., Ltd.
(4) Scanning electron microscope (SEM)
  Apparatus: Inspect S50, manufactured by FEI Company Example 1: Synthesis of Gelators <Synthesis of Aliphatic Aldehyde Having a Hydrocarbon Group (Compound [1]-[3])>

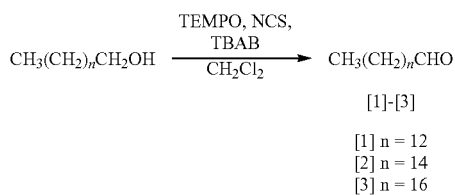

[1] n = 12
[2] n = 14
[3] n = 16

<Synthesis of Compound [1]>

A solution of 100 mL of pure water in which sodium hydrogen carbonate (4.2 g, 50 mmol) and potassium carbonate (0.69 g, 5.0 mmol) were dissolved was added to a solution of 1-tetradecanol (10.7 g, 50 mmol), tetrabutylammonium bromide (TBAB) (0.81 g, 2.5 mmol), and 2,2,6,6-tetramethylpiperidine-1-oxyl (TEMPO) (0.39 g, 2.5 mmol) in 100 mL of dichloromethane and the resultant mixture was stirred at room temperature. To this solution, N-chlorosuccinimide (NCS) (8.0 g, 60 mmol) was added and the resultant mixture was stirred at room temperature for 1 hour. After stirring, an organic phase was separated and the organic phase was washed three times with 100 mL of pure water. After washing, the organic phase was separated and sodium sulfate was added to dry the organic phase. Thereafter, sodium sulfate was removed by filtration and the filtrate was concentrated. The residue was purified by column chromatography (silica gel, hexane:ethyl acetate=100:0 to 95:5 (v/v)) to give the target product 1-tetradecanal (Compound [1]): Yield 77% (8.2 g), $^1$H NMR (400 MHz, CDCl$_3$): δ 9.77 (1H, t, J=1.8 Hz), 2.42 (2H, dt, J=1.8, 7.3 Hz), 1.63 (2H, quintet, J=7.3 Hz), 1.38-1.17 (20H, m), 0.88 (3H, t, J=6.9 Hz).

<Synthesis of Compound [2]>

A solution of 200 mL of pure water in which sodium hydrogen carbonate (8.47 g, 100 mmol) and potassium carbonate (1.42 g, 10.3 mmol) were dissolved was added to a solution of 1-hexadecanol (24.4 g, 100 mmol), tetrabutylammonium bromide (TBAB) (1.67 g, 5.2 mmol), and 2,2,6,6-tetramethylpiperidine-1-oxyl (TEMPO) (0.79 g, 5.1 mmol) in 200 mL of dichloromethane and the resultant mixture was stirred at room temperature. To this solution, N-chlorosuccinimide (NCS) (16.1 g, 120 mmol) was added and the resultant mixture was stirred at room temperature for 1 hour. After stirring, an organic phase was separated and the organic phase was washed three times with 100 mL of pure water. After washing, the organic phase was separated and sodium sulfate was added to dry the organic phase. Thereafter, sodium sulfate was removed by filtration and the filtrate was concentrated. The residue was purified by column chromatography (silica gel, hexane:ethyl acetate=100:0 to 95:5 (v/v)) to give the target product 1-hexadecanal (Compound [2]): Yield 83% (20.0 g), $^1$H NMR (400 MHz, CDCl$_3$): δ 9.76 (1H, t, J=1.8 Hz), 2.42 (2H, dt, J=1.8, 7.3 Hz), 1.63 (2H, quin, J=7.3 Hz), 1.37-1.19 (24H, m), 0.88 (3H, t, J=6.9 Hz).

<Synthesis of Compound [3]>

To a solution of 1-octadecanol (40.6 g, 150 mmol), tetrabutylammonium bromide (TBAB) (2.42 g, 7.5 mmol), and 2,2,6,6-tetramethylpiperidine-1-oxyl (TEMPO) (1.17 g, 7.5 mmol) in 750 mL of dichloromethane, 1.5 L of pure water in which sodium hydrogen carbonate (63.0 g, 750 mmol) and potassium carbonate (10.4 g, 75 mmol) were dissolved was added and the resultant mixture was stirred at room temperature. To this solution, N-chlorosuccinimide (NCS) (22.0 g, 165 mmol) was added and the resultant mixture was stirred at room temperature for 2 hours. After stirring, an organic phase was separated and the organic phase was washed three times with 500 mL of pure water. After washing, the organic phase was separated and sodium sulfate was added to dry the organic phase. Thereafter, sodium sulfate was removed by filtration and the filtrate was concentrated. To the concentrate, 200 mL of acetonitrile was added and the resultant mixture was stirred overnight at room temperature. After stirring, a white powder was obtained by filtration and dried under reduced pressure to give the target product 1-octadecanal (Compound [3]): Yield 86% (34.4 g), $^1$H NMR (500 MHz, CDCl$_3$): δ 9.76 (1H, d, J=1.9 Hz), 2.42 (2H, dt, J=7.3, 1.9 Hz), 1.63 (2H, quintet, J=7.3 Hz), 1.37-1.19 (28H, m), 0.88 (3H, t, J=6.9 Hz).

<Synthesis of Glucose Derivative (Compounds [4]-[8])>

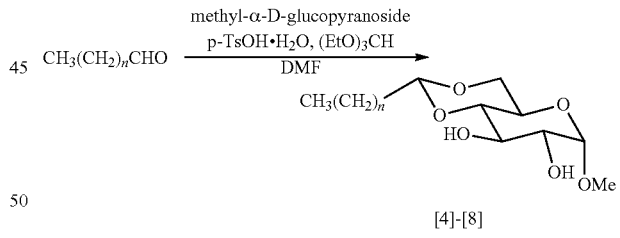

[4]-[8]

[4] n = 9
[5] n = 10
[6] n = 12
[7] n = 14
[8] n = 16

<Synthesis of Compound [4]> p-Toluenesulfonic acid monohydrate (46 mg, 0.24 mmol) and triethyl orthoformate (1.7 mL, 10 mmol) were added to a suspension solution of methyl α-D-glucopyranoside (1.9 g, 10 mmol) in DMF (10 mL) at room temperature. To the resultant suspension solution, a suspension solution of 1-undecanal (1.7 g, 10 mmol) in DMF (5 mL) was added at room temperature. The flask containing a reaction solution was connected to a rotary evaporator. The bath temperature of the rotary evaporator was set at 50° C. and the flask was rotated for 5 hours while the pressure of the inside of the system was being reduced to 50 hPa. After 5 hours, the mixture was allowed to cool to room temperature. A saturated aqueous sodium hydrogen carbonate solution was added to the mixture. The resultant mixture was extracted with ethyl acetate and the extracted liquid was washed with a saturated aqueous sodium chloride solution. After washing, the extracted liquid was dried over sodium sulfate and the sodium sulfate was removed by filtration. Thereafter, the solvent was distilled off under reduced pressure. Hexane was added to the residue and the resultant mixture was stirred while cooling with an ice bath. The obtained suspension was filtered and washed with cold hexane. The obtained powder was dissolved in methanol and recrystallized with water to give the target product (Compound [4]): Yield 33% (1.2 g), $^1$H NMR (400 MHz, CDCl$_3$): δ 4.76 (1H, d, J=4.1 Hz), 4.54 (1H, t, J=5.0 Hz), 4.13 (1H, dd, J=4.8, 10.3 Hz), 3.85 (1H, dt, J=1.8, 9.2 Hz), 3.68-3.54 (2H, m), 3.51 (1H, t, J=10.1 Hz), 3.43 (3H, s), 3.26 (1H, t, J=9.4 Hz), 2.66 (1H, s), 2.23 (1H, d, J=9.6 Hz), 1.72-1.60 (2H, m), 1.45-1.34 (2H, m), 1.34-1.20 (14H, m), 0.88 (3H, t, J=6.9 Hz).

<Synthesis of Compound [5]> p-Toluenesulfonic acid monohydrate (190 mg, 1 mmol), triethyl orthoformate (6.7 mL, 40 mmol), and 1-dodecanal (7.4 g, 40 mmol) were added to a suspension solution of methyl α-D-glucopyranoside (7.8 g, 40 mmol) in DMF (50 mL) at room temperature. The flask containing a reaction solution was connected to a rotary evaporator. The bath temperature of the rotary evaporator was set at 50° C. and the flask was rotated for 6 hours while the pressure of the inside of the system was being reduced to 50 hPa. After 6 hours, the mixture was allowed to cool to room temperature. A saturated aqueous sodium hydrogen carbonate solution was added to the mixture and the resultant mixture was concentrated under reduced pressure. Toluene (200 mL) and water (200 mL) were added to the residue and the resultant mixture was vigorously shaken in a separating funnel. An organic phase was separated and dried over sodium sulfate. The sodium sulfate was removed by filtration and then the solvent was distilled off under reduced pressure. Hexane (200 mL) was added to the residue and the resultant mixture was stirred. The obtained suspension was filtered to give a white solid. Hexane (100 mL) was added to the obtained white solid and the resultant mixture was stirred while cooling with an ice bath. The obtained suspension was filtered and washed with cold hexane. The obtained powder was dried to give the target product (Compound [5]): Yield 63% (9.1 g), $^1$H NMR (400 MHz, CDCl$_3$): δ 4.76 (1H, d, J=4.1 Hz), 4.54 (1H, t, J=5.0 Hz), 4.13 (1H, dd, J=4.8, 10.3 Hz), 3.84 (1H, t, J=9.2 Hz), 3.68-3.54 (2H, m), 3.51 (1H, t, J=10.3 Hz), 3.43 (3H, s), 3.26 (1H, t, J=9.4 Hz), 2.65 (1H, s), 2.22 (1H, d, J=9.6 Hz), 1.70-1.60 (2H, m), 1.44-1.34 (2H, m), 1.34-1.20 (16H, m), 0.88 (3H, t, J=6.9 Hz).

<Synthesis of Compound [6]> p-Toluenesulfonic acid monohydrate (55 mg, 0.29 mmol) and triethyl orthoformate (1.7 mL, 10 mmol) were added to a suspension solution of methyl α-D-glucopyranoside (1.9 g, 10 mmol) in DMF (5 mL) at room temperature. To the resultant suspension solution, a solution of 1-tetradecanal (Compound [1]) (2.1 g, 10 mmol) in DMF (2.5 mL) and hexane (12 mL) was added at room temperature. The flask containing a reaction solution was connected to a rotary evaporator. The bath temperature of the rotary evaporator was set at 40° C. and the flask was rotated for 5 hours while the pressure of the inside of the system was being reduced to 50 hPa. After 5 hours, the resultant mixture was allowed to cool to room temperature. A saturated aqueous sodium hydrogen carbonate solution was added to the mixture and the obtained precipitate was filtered and washed with water. The residue was purified by column chromatography (silica gel, hexane:ethyl acetate=60:40 to 40:60 (v/v)) to give the target product (Compound [6]): Yield 31% (1.2 g), $^1$H NMR (400 MHz, CDCl$_3$): δ 4.78 (1H, d, J=4.1 Hz), 4.54 (1H, t, J=5.0 Hz), 4.12 (1H, dd, J=5.0, 10.1 Hz), 3.85 (1H, t, J=9.2 Hz), 3.68-3.54 (2H, m), 3.50 (1H, t, J=10.3 Hz), 3.43 (3H, s), 3.25 (1H, t, J=9.4 Hz), 2.84 (1H, s), 2.38 (1H, d, J=9.6 Hz), 1.73-1.57 (2H, m), 1.44-1.34 (2H, m), 1.33-1.20 (20H, m), 0.88 (3H, t, J=6.9 Hz).

<Synthesis of Compound [7]> p-Toluenesulfonic acid monohydrate (25 mg, 0.13 mmol) and triethyl orthoformate (0.7 mL, 4 mmol) were added to a suspension solution of methyl α-D-glucopyranoside (0.8 g, 4 mmol) in DMF (5 mL) at room temperature. To the resultant suspension solution, a solution of 1-hexadecanal (Compound [2]) (1.0 g, 4 mmol) in dichloromethane (5 mL) was added at room temperature. The flask containing a reaction solution was connected to a rotary evaporator. The bath temperature of the rotary evaporator was set at 40° C. and the flask was rotated for 4 hours while the pressure of the inside of the system was being reduced to 50 hPa. After 4 hours, the resultant mixture was allowed to cool to room temperature. A saturated aqueous sodium hydrogen carbonate solution was added to the mixture and the obtained precipitate was filtered and washed with water. The residue was purified by column chromatography (silica gel, hexane: ethyl acetate=60:40 to 40:60 (v/v)) to give the target product (Compound [7]): Yield 21% (0.35 g)$^1$H NMR (400 MHz, CDCl$_3$): δ 4.76 (1H, d, J=3.7 Hz), 4.54 (1H, t, J=5.0 Hz), 4.12 (1H, dd, J=4.8, 10.3 Hz), 3.85 (1H, t, J=9.4 Hz), 3.68-3.54 (2H, m), 3.51 (1H, t, J=10.3 Hz), 3.43 (3H, s), 3.26 (1H, t, J=9.4 Hz), 2.72 (1H, s), 2.28 (1H, s), 1.71-1.60 (2H, m), 1.44-1.34 (2H, m), 1.33-1.21 (24H, m), 0.88 (3H, t, J=6.9 Hz).

<Synthesis of Compound [8]-1>

Triethyl orthoformate (14.7 mL, 100 mmol) was added to a suspension solution of methyl α-D-glucopyranoside (19.4 g, 100 mmol), 1-octadecanal (Compound [3]) (29.5 g, 110 mmol), and p-toluenesulfonic acid monohydrate (1.05 g, 5.5 mmol) in DMF (130 mL) at room temperature. The flask containing a reaction solution was connected to a rotary evaporator. The bath temperature of the rotary evaporator was set at 70° C. and the flask was rotated for 5 hours while the pressure of the inside of the system was being reduced to 220 hPa. After 5 hours, the mixture was allowed to cool to room temperature. 13.3 mL of triethylamine was added to the mixture and the reaction solvent was distilled off under reduced pressure. To the residue, 350 mL of ethanol was added to carry out solid-liquid washing. After filtration, white powder was dried under reduced pressure. This washing operation was carried out two times to give the target product (Compound [8]): Yield 76% (33.7 g)$^1$H NMR (400 MHz, CDCl$_3$): δ 4.76 (1H, d, J=3.7 Hz), 4.54 (1H, t, J=4.6 Hz), 4.13 (1H, dd, J=5.0, 10.1 Hz), 3.86 (1H, t, J=9.2 Hz), 3.69-3.54 (2H, m), 3.51 (1H, t, J=10.1 Hz), 3.43 (3H, s), 3.26 (1H, t, J=9.2 Hz), 2.73 (1H, br s), 2.30 (1H, br s), 1.76-1.55 (2H, m), 1.50-1.14 (30H, m), 0.88 (3H, t, J=6.4 Hz).

<Synthesis of Compound [8]-2>

Triethyl orthoformate (1.7 mL, 10 mmol) was added to a suspension solution of methyl α-D-glucopyranoside (1.9 g, 10 mmol), 1-octadecanal (Compound [3]) (2.7 g, 10 mmol), and p-toluenesulfonic acid monohydrate (105 mg, 0.55 mmol) in DMF (10 mL) at room temperature. The flask containing a reaction solution was connected to a rotary evaporator. The bath temperature of the rotary evaporator was set at 70° C. and the flask was rotated for 5 hours while the pressure of the inside of the system was being reduced to 220 hPa. After 5 hours, the resultant mixture was allowed to cool to room temperature. A saturated aqueous sodium hydrogen carbonate solution was added to the mixture and the obtained precipitate was filtered and washed with water (50 mL) two times. To the obtained residue, hexane (30 mL) was added to carry out solid-liquid washing. After filtration, white powder was dried under reduced pressure to give the target product (Compound [8]): Yield 70% (3.1 g).

<Synthesis of Glucose Derivative (Compound [9])>

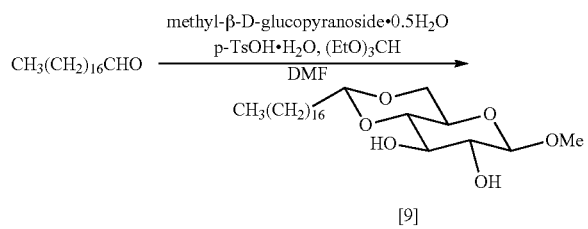

Triethyl orthoformate (2.5 mL, 15 mmol) was added to a suspension solution of methyl β-D-glucopyranoside 0.5 hydrate (2.0 g, 10 mmol), 1-octadecanal (Compound [3]) (2.7 g, 10 mmol), and p-toluenesulfonic acid monohydrate (105 mg, 0.55 mmol) in DMF (10 mL) at room temperature. The flask containing a reaction solution was connected to a rotary evaporator. The bath temperature of the rotary evaporator was set at 70° C. and the flask was rotated for 5 hours while the pressure of the inside of the system was being reduced to 220 hPa. After 5 hours, the resultant mixture was allowed to cool to room temperature. A saturated aqueous sodium hydrogen carbonate solution was added to the mixture and the obtained precipitate was filtered and washed with water (50 mL) two times. To the obtained residue, diethyl ether (30 mL) was added to carry out solid-liquid washing. After filtration, white powder was dried under reduced pressure to give the target product (Compound [9]): Yield 81% (3.6 g) $^1$H NMR (400 MHz, CDCl$_3$): δ 4.55 (1H, d, J=5.0 Hz), 4.28 (1H, t, J=7.8 Hz), 4.23-4.14 (1H, m), 3.80-3.69 (1H, m), 3.61-3.50 (4H, m), 3.48-3.40 (1H, m), 3.36-3.25 (2H, m), 2.73 (1H, d, J=2.3 Hz), 2.62 (1H, d, J=2.3 Hz), 1.74-1.56 (4H, m), 1.47-1.16 (30H, m), 0.88 (3H, t, J=6.4 Hz).

<Synthesis of Glucose Derivative (Compound [10])>

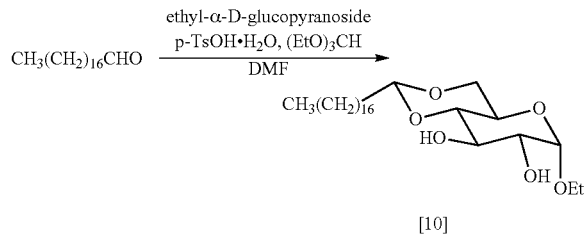

Triethyl orthoformate (1.7 mL, 10 mmol) was added to a suspension solution of ethyl α-D-glucopyranoside (2.1 g, 10 mmol), 1-octadecanal (Compound [3]) (2.7 g, 10 mmol), and p-toluenesulfonic acid monohydrate (105 mg, 0.55 mmol) in DMF (10 mL) at room temperature. The flask containing a reaction solution was connected to a rotary evaporator. The bath temperature of the rotary evaporator was set at 70° C. and the flask was rotated for 5 hours while the pressure of the inside of the system was being reduced to 220 hPa. After 5 hours, the resultant mixture was allowed to cool to room temperature. A saturated aqueous sodium hydrogen carbonate solution was added to the mixture and the obtained precipitate was filtered and washed with water (50 mL) two times. To the obtained residue, diethyl ether (30 mL) was added to carry out solid-liquid washing. After filtration, white powder was dried under reduced pressure to give the target product (Compound [10]): Yield 74% (3.4 g) $^1$H NMR (400 MHz, CDCl$_3$): δ 4.87 (1H, d, J=4.1 Hz), 4.54 (1H, t, J=5.0 Hz), 4.11 (1H, dd, J=4.6, 10.1 Hz), 3.90-3.73 (2H, m), 3.67 (1H, dt, J=4.6, 10.1 Hz), 3.60-3.45 (3H, m), 3.26, (1H, t, J=9.6 Hz), 2.65 (1H, s), 2.20 (1H, d, J=10.1 Hz), 1.75-1.53 (5H, m), 1.46-1.15 (32H, m), 0.88 (3H, t, J=6.9 Hz).

<Synthesis of Mannose Derivative (Compound [11])>

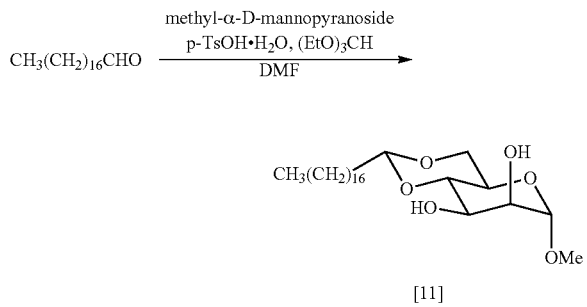

Triethyl orthoformate (1.7 mL, 10 mmol) was added to a suspension solution of methyl α-D-mannopyranoside (1.9 g, 10 mmol), 1-octadecanal (Compound [3]) (2.7 g, 10 mmol), and p-toluenesulfonic acid monohydrate (105 mg, 0.55 mmol) in DMF (10 mL) at room temperature. The flask containing a reaction solution was connected to a rotary evaporator. The bath temperature of the rotary evaporator was set at 70° C. and the flask was rotated for 5 hours while the pressure of the inside of the system was being reduced to 220 hPa. After 5 hours, the resultant mixture was allowed to cool to room temperature. A saturated aqueous sodium hydrogen carbonate solution was added to the mixture and the obtained precipitate was filtered and washed with water (50 mL) two times. To the obtained residue, diethyl ether (30 mL) was added to carry out solid-liquid washing. After filtration, white powder was dried under reduced pressure. The obtained solid was purified by column chromatography (silica gel, hexane: ethyl acetate=80:20 to 50:50 (v/v) and chloroform: ethyl acetate=50:50 (v/v)) to give the target product (Compound [11]): Yield 27% (1.2 g) $^1$H NMR (400 MHz, CDCl$_3$): δ 4.74 (1H, d, J=1.4 Hz), 4.58 (1H, t, J=5.0 Hz), 4.17-4.07 (1H, m), 4.05-3.94 (2H, m), 3.71-3.56 (3H, m), 3.37 (3H, s), 2.55 (1H, d, J=2.3 Hz), 2.51 (1H, d, J=3.7 Hz), 1.69-1.60 (2H, m), 1.47-1.17 (30H, m), 0.88 (3H, t, J=6.9 Hz).

<Synthesis of Galactose Derivative (Compound [12])>

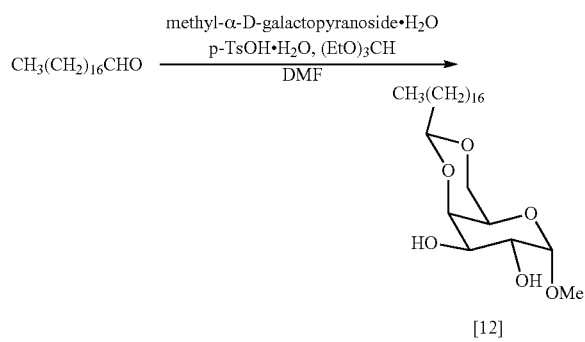

Triethyl orthoformate (3.3 mL, 20 mmol) was added to a suspension solution of methyl α-D-galactopyranoside monohydrate (2.1 g, 10 mmol), 1-octadecanal (Compound [3]) (2.7 g, 10 mmol), and p-toluenesulfonic acid monohydrate (105 mg, 0.55 mmol) in DMF (10 mL) at room temperature. The flask containing a reaction solution was connected to a rotary evaporator. The bath temperature of the rotary evaporator was set at 70° C. and the flask was rotated for 5 hours while the pressure of the inside of the system was being reduced to 220 hPa. After 5 hours, the mixture was allowed to cool to room temperature. A saturated aqueous sodium hydrogen carbonate solution was added to the mixture. The resultant mixture was extracted with ethyl acetate and the extracted liquid was washed with a saturated aqueous sodium chloride solution. An organic phase was separated and sodium sulfate was added to dry the organic phase. Thereafter, sodium sulfate was removed by filtration and the filtrate was concentrated. To the residue, hexane (30 mL) was added to carry out solid-liquid washing. After filtration, white powder was dried under reduced pressure. The residue was purified by column chromatography (silica gel, hexane:ethyl acetate=60:40 to 40:70 (v/v)) to give the target product (Compound [12]): Yield 55% (2.4 g)$^1$H NMR (400 MHz, CDCl$_3$): δ 4.90 (1H, d, J=3.2 Hz), 4.57 (1H, t, J=5.0 Hz), 4.12 (1H, d, J=12.4 Hz), 4.03 (1H, t, J=3.7 Hz), 3.92-3.73 (3H, m), 3.60 (1H, s), 3.44 (3H, s), 2.37 (1H, d, J=7.8 Hz), 2.10 (1H, d, J=7.8 Hz) 1.76-1.65 (2H, m), 1.50-1.15 (30H, m), 0.88 (3H, t, J=6.0 Hz).

Example 2: Gel Forming Ability Test of Gelators

The gel forming ability to various solvents was evaluated using Compounds [4]-[12] synthesized in Example 1 as gelators.

The gelation test was carried out as follows. A gelator and a solvent were added to a 4 mL screw thread sample tube. In the case of Compounds [4] to [7], the sample containing each of octane, squalane, squalene, isopropyl myristate (IPM), olive oil, KF995 (decamethylcyclopentasiloxane), and ethylene glycol was heated at 120° C., the sample containing each of jojoba oil, toluene, and water was heated at 100° C., the sample containing each of cyclohexane, ethyl acetate, acetonitrile, DMSO (dimethylsulfoxide), ethanol, mixed solvents (75% of ethanol (ethanol/water=75/25), 50% of ethanol (ethanol/water=50/50), and 25% of ethanol (ethanol/water=25/75) was heated at 80° C., and containing each of chloroform and methanol was heated at 60° C. Each sample was heated for 30 minutes. On the other hand, in the case of Compounds [8] to [12], the sample containing each of octane, squalane, squalene, isopropyl myristate (IPM), olive oil, jojoba oil, KF995 (decamethylcyclopentasiloxane), toluene, ethylene glycol, and water was heated at 100° C., the sample containing each of cyclohexane, ethyl acetate, acetonitrile, DMSO (dimethylsulfoxide), ethanol, the mixed solvents (75% of ethanol (ethanol/water=75/25), 50% of ethanol (ethanol/water=50/50), and 25% of ethanol (ethanol/water=25/75) was heated at 80° C., and the sample containing each of chloroform and methanol was heated at 60° C. Each sample was heated for 30 minutes.

Each of the obtained solutions was cooled to room temperature and allowed to stand for 1 hour to observe the formation of a gel (in the case of using toluene and ethyl acetate, these samples were left for 24 hours (left to cool) depending on the kind of Compounds). After the mixture was allowed to stand to cool, a state in which the fluidity of the solution was lost and the solution did not flow down even when the sample tube was turned upside down was determined as "gelation". The gelation test was carried out at the concentration of the gelator: 5.0, 4.0, 3.0, 2.0, 1.0, 0.5, 0.25, or 0.1 wt % and the lowest concentration (wt %) of gelator required for gelation was determined to be the lowest gelation concentration. Here, wt % indicating the unit of concentration means wt/vol×100. The obtained results are listed in Table 1. The values in Table 1 are the lowest gelation concentration (wt %) and signs in Table 1 are the states of the formed gel (hereinafter, the other tables in this specification have the same description). The state of the formed gel was evaluated as "G" in the case of a transparent gel, "TG" in the case of a translucent gel, "OG" in the case of an opaque gel, "P-G" in the case of partially forming a transparent gel, "P-TG" in the case of partially forming a translucent gel, "P-OG" in the case of partially forming an opaque gel, "S" in the case that the solution was as it was, "P" in the case that precipitate was generated, and "IS" in the case that the gelator was not dissolved even when the mixture was heated and thus determined to be insoluble. Solvents not evaluated were marked as "-".

TABLE 1

Results of gelation test of sugar derivative type gelators (Compounds [4]-[12])

| Solvent | Compound [4] | Compound [5] | Compound [6] | Compound [7] | Compound [8] | Compound [9] | Compound [10] | Compound [11] | Compound [12] |
|---|---|---|---|---|---|---|---|---|---|
| Octane | 0.5 G | 1 G | 1 TG | 0.25 TG | 2 TG | 0.5 TG | 2 OG | 2 G | 2 OG |
| Cyclohexane | S | S | S | 1 TG | 2 P-TG | 0.1 TG | 2 P-OG | 3 TG | 3 OG |
| Squalane | 0.25 G | 0.25 G | 1 TG | 0.25 G | 0.25 TG | 0.05 G | 0.25 G | 0.1 G | 1 TG |
| Squalene | — | — | — | — | 5 TG | 0.1 G | 1 G | 0.5 G | 1 TG |
| Jojoba oil | 2 G | 1 G | 0.5 G | 0.5 G | 0.25 G | 0.25 G | 0.25 G | 1 G | 0.5 OG |
| IPM | S | S | 2 TG | 2 TG | 2 TG | 0.5 TG | 2 OG | 2 G | 3 OG |
| Olive oil | 5 G | 5 G | 2 TG | 2 TG | 2 TG | 0.5 G | 2 TG | 2 G | 2 OG |
| KF995 | 0.25 G | 0.1 G | 0.25 G | 0.25 TG | 0.25 P-TG | 0.25 G | 0.5 TG | 0.25 G | 1 OG |

TABLE 1-continued

Results of gelation test of sugar derivative type gelators (Compounds [4]-[12])

| Solvent | Compound [4] | Compound [5] | Compound [6] | Compound [7] | Compound [8] | Compound [9] | Compound [10] | Compound [11] | Compound [12] |
|---|---|---|---|---|---|---|---|---|---|
| Toluene | S | S | S | 5 G | 5 P-G* | 1 G | 5 P-OG* | 5 P-OG* | 5 P-TG* |
| Chloroform | — | — | — | — | S | S | S | S | S |
| Ethyl acetate | — | — | — | — | S | 5 OG | S | S | 5 OG* |
| Acetonitrile | S | S | S | 2 OG | 5 P-TG | 0.5 G | 3 OG | P | 2 OG |
| DMSO | S | S | S | S | P | 3 TG | 4 OG | S | 3 TG |
| Ethylene glycol | 5 OG | 5 TG | 1 TG | 0.5 TG | 0.5 TG | 0.02 G | 4 OG | 0.05 TG | P |
| Methanol | — | — | — | — | P | 3 TG | 3 OG | 2 OG | 3 OG |
| Ethanol | S | S | S | S | P | 3 TG | P | P | 3 P-TG |
| 75% Ethanol | P | S | S | P | 2 P-OG | 0.5 TG | 1 OG | 5 OG | 2 TG |
| 50% Ethanol | P | P | 0.5 TG | 0.1 G | 0.1 TG | 0.05 G | 0.05 TG | 3 OG | 1 OG |
| 25% Ethanol | IS | 0.1 G | 0.1 TG | 2 P-OG | IS | P | 5 P-OG | P | P |
| Water | 0.1 P-TG | 1 OG | IS | IS | IS | P | P | P | IS |

The mark "*" means the result after stand to cool for 24 hours.

As shown in Table 1, it was clear that the sugar derivative type gelators (Compounds [4]-[12]) indicated gelation ability for a wide range of solvent groups from nonpolar solvents to protic solvents and Compounds [4]-[12] functioned as low molecular-weight gelators.

KF995 gel formed by blending the glucose derivative: Compound [8] in an amount of 2 wt % had self-sustainable hardness (self-supporting property) (refer to FIG. 1).

Example 3: Thixotropy Test

The thixotropy of various gels including the glucose derivative type gelator (Compound [8]) was evaluated. The thixotropy test was carried out as follows. Gels were prepared with the concentration of the gelator being changed in the same method as the method in Example 2. Thereafter, the gel was disintegrated by shaking the obtained gel from a gel state to a sol state using a vortex mixer and the resultant sol was allowed to stand for a certain period of time (1.5 hours) at room temperature. After being allowed to stand for the certain period of time, the sample tube containing the solution was turned upside down and the sample was determined to be "thixotropic" when the solution did not flow down. The lowest concentration (wt %) of the gelator determined to have thixotropy is listed in Table 2.

TABLE 2

Results of thixotropy test of glucose derivative type gelator (Compound [8])

| Squalane | Jojoba oil | KF995 | Olive oil | Ethanol/water (50/50)(vol/vol) |
|---|---|---|---|---|
| 0.25 | 0.25 | 1.0 | 2.0 | 0.1 |

* The values in the table indicate the lowest concentration (wt %) of the gelator (Compound) required for gelation of each solvent in which thixotropy is determined.

As shown in Table 2, formation of the thixotropic gel of the glucose derivative type gelator (Compound [8]) of the present invention was determined.

Example 4: Additive Blending Test <Gelation Test (1) at the Time of Blending Surfactant>

In general, various additives such as surfactants are blended in cosmetics and quasi-drugs. A gelator having gelation ability even when such additives are blended and, in particular, a gelator having gelation ability at the time of blending a surfactant can be expected for easily preparing a water-oil dispersion gel as described below. Consequently, such a gelator is remarkably useful because it can be assumed that various applications are developed by using the gelator.

Furthermore, one gelator is expected for preparing both O/W dispersion gel and W/O dispersion gel, if the gelator can form the gel of the surfactant-containing solution regardless of the magnitude of the HLB value.

Hereinafter, the gelation ability of the gelator of the present invention was examined when Tween 20 (HLB=16.7) having a large HLB value or Span 80 (HLB=4.3) having a small HLB value was blended.

<Surfactant Blending Test>

The gelation test at the time of blending the surfactant was carried out as follows.

The gelation ability when polyoxyethylene (20) sorbitan monolaurate (Tween 20) (HLB=16.7) being a nonionic surfactant was added was examined. First, Tween 20 was dissolved in water to prepare an aqueous solution containing 1 wt % of Tween 20. Thereafter, the glucose derivative type gelator (Compound [8]) was added to a 4 mL screw tube so that the concentration of the gelator reached the predetermined concentration. The previously prepared surfactant blended aqueous solution was added and the resultant mixture was heated at 100° C. for 30 minutes. The obtained solution was cooled to room temperature and allowed to stand for 1 hour. The formation of gel was determined by turning the screw tube upside down. The results are listed in Table 3.

Subsequently, the gelation ability was examined when Span 80 (HLB=4.3) being a nonionic surfactant was added. Span 80 was poured into a 4 mL screw tube so that the concentration of Span 80 reached the predetermined concentration (0.5 wt %) and the glucose derivative type gelator (Compound [8]) was poured into the 4 mL screw tube so as that the concentration of the gelator reached the predetermined concentration. Each of oil agents (squalane, olive oil, jojoba oil, and KF995) was added and the resultant mixture was heated at 120° C. for 30 minutes. The obtained solution was cooled to room temperature and allowed to stand for 1 hour. The formation of gel was determined by turning the screw tube upside down. The results are listed in Table 3.

TABLE 3

Results of gelation test at the time of blending surfactant (1)

| Blending 1 wt % of Tween 20 Water | Blending 0.5 wt % of Span 80 | | | |
|---|---|---|---|---|
| | Squalane | Olive oil | Jojoba oil | KF995 |
| 4.0 | 1.0 | 1.0 | 2.0 | 2.0 |
| OG | TG | G | TG | OG |

* The values in the table indicate the lowest concentration (wt %) of the gelator (Compound) required for forming the gel of each solvent.
* G: Transparent gel, TG: Translucent gel, and OG: Opaque gel.

As shown in Table 3, the gelator of the present invention gave a result that a hydrogel was capable of being formed when Tween 20 being a nonionic surfactant was blended.

As shown in above Table 1, the glucose derivative type gelator of Compound [8] alone cannot form a hydrogel (a gel containing 100% of water as a solvent) and hydrogel formation by using a combination of the gelator and the surfactant can be said to be a remarkably distinctive example.

As shown in Table 3, formation of gels was determined in every oil agent at the time of blending Span 80. This result suggested that W/O type dispersion gels be possibly formed at the time of preparation of the water-oil dispersion gel.

Example 5: Additive Blending Test <Gelation Test (2) at the Time of Blending Surfactant>

In this Example, gelation ability of the gelator of the present invention was examined when the nonionic surfactant (Tween 20), the anionic surfactants [sodium di(2-ethylhexyl)sulfosuccinate (AOT) and sodium dodecyl sulfate (SDS)], and cationic surfactants [cetyltrimethylammonium bromide (CTAB) and cetylpyridinium chloride (CPC)] were blended as various surfactants.

First, each of the above various surfactants was dissolved in water to prepare 0.5 wt % of an aqueous solution containing each of various surfactants. Thereafter, the glucose derivative type gelator (Compound [8]) was poured into a 4 mL screw tube so that the concentration of the gelator reached the predetermined concentration. The previously prepared surfactant blended aqueous solution was added and the resultant mixture was heated at 100° C. for 30 minutes. The obtained solution was cooled to room temperature and allowed to stand for 1 day (in the case of Tween 20, for 1 hour) and the formation of gel was determined by turning the screw tube upside down. The results are listed in Table 4.

TABLE 4

Results of gelation test at the time of blending surfactant (2)

| Nonionic surfactant | Anionic surfactant | | Cationic surfactant | |
|---|---|---|---|---|
| Tween 20 | AOT | SDS | CTAB | CPC |
| 5 OG* | 2 TG | 1 TG | 1 TG | 1 TG |

*1 hour later after standing to cool at room temperature.
*The values in the table indicate the lowest concentration (wt %) of the gelator (Compound) required for forming the gel of each solvent.
*TG: Translucent gel and OG: Opaque gel.

As shown in Table 4, the gelator of the present invention gave a result that the gelator of the present invention can form hydrogels in any cases where the nonionic surfactant, the anionic surfactants, or the cationic surfactants are blended.

Example 6: Water-Oil Dispersion Test Using Glucose Derivative Type Gelator (Compound [8])

Emulsion preparation technology for uniformly dispersing and stabilizing an oil agent and water has been required for various applications such as cosmetics, pharmaceutical products, foods, and functional materials.

Reduction in coalescence of droplets by gelation of a continuous phase is one of important factors in stabilization of emulsion. In other words, induction of gelation of the continuous phase in the W/O emulsion and the O/W emulsion caused by a certain gelator means that the gelator can possibly stabilize the W/O or O/W emulsion.

In Examples 4 and 5, it was determined that the hydrogel (a gel containing 100% of water as a solvent) was capable of being formed by addition of a small amount of surfactant Tween 20 in addition to the fact that the gelator has gel forming ability even at the time of surfactant blending. In Example 2, the gelator of the present invention has obtained the result that the gelator has gel forming ability for both of the hydrophobic organic solvent (oil agent) and the alcohol blended aqueous solution (ethanol/water solution). This result suggests that the gelator of the present invention be capable of uniformly dispersing and stabilizing water and oil without using a surfactant.

Therefore, in this Example, in order to determine that the gelator of the present invention can uniformly disperse both solvents of water and oil agent, the water-oil dispersion test was carried out.

<Water-KF995 Dispersion Gel Preparation Test>

The water-oil dispersion test was carried out as follows. A glucose derivative type gelator (Compound [8]), an oil agent (KF995), and water were poured into a 4 mL screw thread sample tube so that the concentrations of these components reached the predetermined concentrations. In the surfactant blended example, in the case of Tween 20, 1 wt % of a Tween 20 aqueous solution was used instead of water and, in the case of Span 80, Span 80 was added at the time of adding the gelator so that the concentration of Span 80 was 1 wt % (with the proviso that, only in the case of KF995/water (2/8 (vol/vol)), the concentration of Span 80 was 0.5 wt %).

The sample tube containing the mixed solution including the gelator and other components was heated for 30 minutes to dissolve the mixed components. Thereafter, shearing with a vortex mixer was applied to the dissolved mixture. The resultant mixture was allowed to stand at room temperature for 1 hour to observe the dispersion state. A state where, after the mixture was allowed to stand to cool, the fluidity of the solution was lost and the solution did not flow down even when the sample tube was turned upside down and where the water and oil were uniformly dispersed were determined to be a "water/oil dispersion gel". The obtained results are listed in Table 5.

TABLE 5

Results of water-KF995 dispersion gel preparation test of glucose derivative type gelator [Compound [8]]

| Gelator | | Compound [8] | | |
|---|---|---|---|---|
| Additive | | None | Tween 20 | Span 80 |
| KF995/water (vol/vol) | 7/3 | 0.1 (100° C., 3 minutes) | 2.0 (100° C., 3 minutes) | 2.0 (80° C., 2 minutes) |
| | 5/5 | 0.1 (100° C., 3 minutes) | 2.0 (100° C., 3 bminutes) | 2.0 (80° C., 2 minutes) |

TABLE 5-continued

Results of water-KF995 dispersion gel preparation test of glucose derivative type gelator [Compound [8]]

| Gelator | Compound [8] | | |
|---|---|---|---|
| Additive | None | Tween 20 | Span 80 |
| 3/7 | 0.1 (100° C., 3 minutes) | 2.0 (100° C., 3 minutes) | 2.0 (80° C., 0.5 minute) |
| 2/8 | | 2.0 (100° C., 3 minutes) | 0.5 (80° C., 0.5 minute) |

* The values in the table indicate the concentration (wt %) of the gelator (Compound) required for forming the gel of each solvent.
* The values in parentheses in the table indicate the heating temperature (° C.) and the shearing time (minutes) by the vortex mixer.
* The diagonal line indicates that the test was not carried out.

As shown in Table 5, the water/oil dispersion gel was capable of being formed in both cases where the gelator (Compound [8]) was used alone and where the gelator and the surfactants (Tween 20 and Span 80) were used in combination in the preparation of the water-KF995 dispersion gel.

<Identification of Dispersed Phase and Continuous Phase of Dispersion Gel Using Confocal Laser Scanning Microscope>

Figure 2:
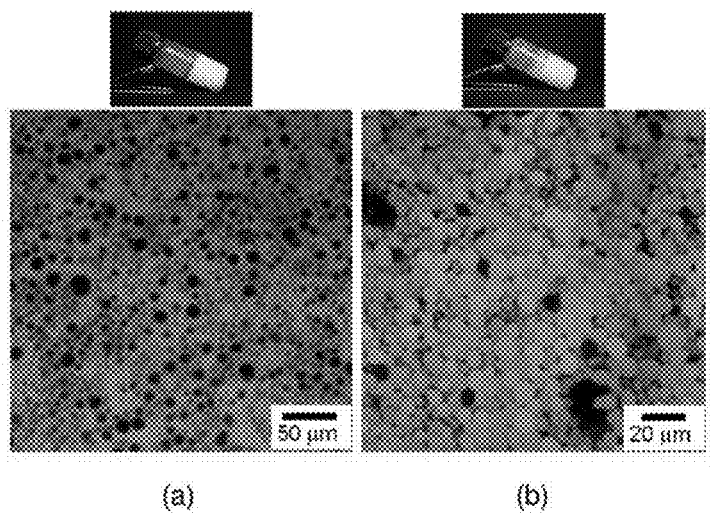
FIG. 2A and FIG. 2B are photographs illustrating gel appearances and confocal laser scanning microscopic images of the gel of water/KF995 (KF995/water=2/8 (vol/vol)) to which Tween 20 is blended (FIG. 2A) and gel of water/KF995 (KF995/water=2/8 (vol/vol)) to which Span 80 is blended (FIG. 2B) prepared in Example 6 using Compound [8] as a gelator.

FIG. 2 illustrates the results of confocal laser scanning microscopic observation of a water/oil dispersion gel prepared by blending the surfactant in the same manner as above except that 5 µM of an aqueous solution of uranine was used as a fluorescent dye instead of water. As the water/oil dispersion gel, a dispersion gel of water-KF995 (KF995/water=2/8 (vol/vol)) was used (refer to Table 5 for the addition amount of the gelator) and Tween 20 was blended at 1 wt % or Span 80 was blended at 1 wt % as the surfactant. In FIG. 2, the phase of emitting the fluorescent color (the phase of appearing white on the image) is the aqueous phase.

As shown in FIG. 2A, it was determined the water-KF995 (KF995/water=2/8 (vol/vol)) dispersion gel blended with 1 wt % of Tween 20 was an O/W emulsion gel (the dispersed phase was the KF995 phase and the continuous phase was the water phase), whereas the water-KF995 (KF995/water=2/8 (vol/vol)) dispersion gel containing 1.0 wt % of Span 80 was a W/O emulsion gel (the dispersed phase was the water phase and the continuous phase was the KF995 phase).

As shown in the results of Example 2, among the gelators of the present invention, Compound [8] and the like do not have gelation ability to 100% of water. However, it has been determined in Example 4 and Example 5 that hydrogels can be formed by blending the surfactant such as Tween 20 to this system. The result of forming the O/W emulsion gel suggests that the complex of the glucose derivative type gelator (Compound [8]) and Tween 20 be involved in emulsion gel formation.

The W/O emulsion gel having a high water content is generally expected to be applied to products in cosmetic application, which do not flow with sweat or water, spread easily on skin, and satisfy both fresh feeling of use and water resistance. However, it has been known that the emulsion is unstable.

The result that the high water content W/O emulsion, which is considered to be difficult to prepare, is obtained as the emulsion gel when the gelator of the present invention is used and Span 80 is blended as a surfactant can be said to be one of the major characteristics obtained by the gelator of the present invention.

<Test for Preparing Water-Squalane, Water-IPM, and Water-Jojoba Oil Dispersion Gels of Glucose Derivative Type Gelator (Compound [8])>

Subsequently, using the gelator (Compound [8]) of the present invention and using squalane, IPM, or jojoba oil as an oil agent, the water-oil dispersion gel preparation test was carried out in accordance with the procedure <Water-KF995 dispersion gel preparation test> described above.

The obtained results are listed in Table 6.

TABLE 6

Water-oil dispersion gel preparation test of glucose derivative type gelator (Compound [8])

| | | Squalane/water (vol/vol) | | | Jojoba oil/water (vol/vol) | | | IPM/water (vol/vol) | | |
|---|---|---|---|---|---|---|---|---|---|---|
| | | 3/7 | 2/8 | 1/9 | 3/7 | 2/8 | 1/9 | 3/7 | 2/8 | 1/9 |
| Additive | None | 2.0 | | | 2.0 | | | 1.0 | | |
| | Tween 20 | 2.0 | 2.0 | 2.0 | 2.0 | 2.0 | 2.0 | 2.0 | 2.0 | 2.0 |
| | Span 80 | 0.5 | 0.5 | | 0.5 | | | 1.0 | 1.0 | |

* The values in the table indicate the concentration (wt %) of the gelator (Compound) required for forming the gel of each solvent.
* In case of no additives, the heating temperature is 80° C. and the shearing time by the vortex mixer is 5 minutes.

When Tween 20 is added, the heating temperature is 100° C. and the shearing time by vortex mixer is 3 minutes.

When Span 80 is added, the heating temperature is 80° C. and the shearing time by the vortex mixer is 5 minutes.

Tween 20 was used as 1 wt % of a Tween 20 solution.

Span 80 was added directly so that the concentration of Span 80 reached 0.5 wt % when the gelator was added.

The diagonal lines indicate that the test was not carried out.

As can be seen from Table 6, it was determined that the water-oil dispersion gels were capable of being prepared in various oily base materials when the gelator (Compound [8]) was used alone, when the gelator and Tween 20 were used in combination, and when the gelator and Span 80 were used in combination. This result suggests that the glucose derivative type gelator (Compound [8]) enable the water-oil dispersion gels of various oily base materials to be prepared.

<Preparation of Water-Soluble Drug-Containing Water-Oil Dispersion Gel>

Subsequently, preparation of water-oil dispersion gels using water-soluble drug aqueous solutions instead of water was carried out. The water-oil dispersion gel preparation test was carried out in accordance with the procedure in <Water-KF995 dispersion gel preparation test> described above by using L-ascorbic acid (20% of an aqueous solution (pH 2.0)), L-ascorbic acid 2-phosphate trisodium salt (40% of an aqueous solution (pH 8.4)), glycine (18% of an aqueous solution (pH 6.1)), D-(+)-glucosamine hydrochloride (25% of an aqueous solution (pH 7.1)) as the water soluble drugs, using 0.5 wt % of a glucose derivative type gelator (Compound [8]), 0.5 wt % of Span 80, and KF995 as an oily base material, at the ratio of the water soluble liquid and the oily base material to be 80/20, and using these water soluble drugs as aqueous solutions having predetermined concentrations listed in the parentheses. The obtained results are listed in Table 7.

TABLE 7

Preparation test of water-oil dispersion
gel containing water-soluble drug

| L-Ascorbic acid | L-Ascorbic acid 2-phosphate trisodium salt | Glycine | Glucosamine |
| --- | --- | --- | --- |
| ○ (0.5 minute) | ○ (0.5 minute) | ○ (1 minute) | ○ (0.5 minute) |

* The values in parentheses in the table indicate the shearing time (minutes) by the vortex mixer.

As can be seen from Table 7, stable water-oil dispersion gels were capable of being prepared even when any one of the water-soluble drugs was contained. The L-ascorbic acid aqueous solution is acidic (pH about 2.0) and the L-ascorbic acid-2-phosphate trisodium salt aqueous solution is basic (pH about 8.4), and thus it was determined that the water-oil dispersion gels were capable of being prepared in a wide pH range.

Example 7: SEM Observation of Various Gels

<SEM observation of KF995 xerogel and 50% of EtOH gel of glucose derivative type gelator (Compound [8])>

A KF995 gel was prepared by adding 0.25 wt % of the gelator (Compound [8]) prepared in Example 1. Thereafter, the xerogel obtained by vacuum-drying the prepared gel on a carbon tape for 24 hours was observed with the scanning electron microscope (SEM).

Furthermore, 50% of ethanol gel (ethanol/water=50/50 (vol/vol)) to which 0.1 wt % of the gelator was added was prepared. Thereafter, the gel was placed on a carbon tape and dried under reduced pressure of 80 Pa to observe with SEM.

Figure 3:
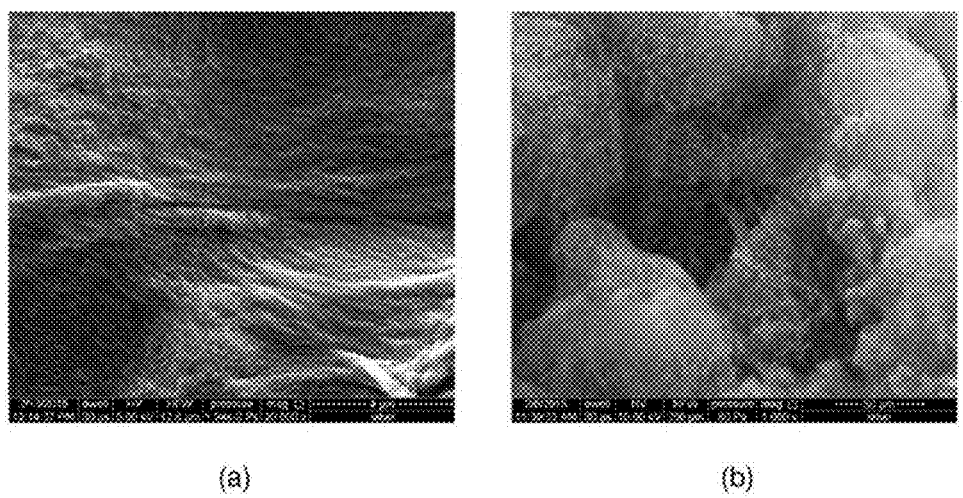
FIG. 3A and FIG. 3B are views illustrating scanning micrographs of a KF995 xerogel (FIG. 3A) and 50% of ethanol gel (FIG. 3B) prepared in Example 7 using Compound [8] as a gelator.

The obtained results are illustrated in FIG. 3 (FIG. 3A: KF995 xerogel, FIG. 3B: 50% of ethanol gel).

From the SEM images illustrated in FIG. 3, fiber-like images were obtained from both KF995 xerogel (FIG. 3A) and 50% of EtOH gel (FIG. 3B) formed using the gelator (Compound [8]). From this observation, it was determined that the gel including the glucose derivative type gelator (Compound [8]) had a three-dimensional network structure.

<SEM observation of water-KF995 dispersion gel containing 1% of Tween 20 and a glucose derivative type gelator (Compound [8])>

Subsequently, a water-KF995 dispersion gel containing 1% of Tween 20, which was prepared using the gelator (Compound [8]) prepared in Example 1, was observed with SEM.

The water-KF995 dispersion gel was prepared by using 2 wt % of the gelator and blending 1% of Tween 20. Thereafter, the gel was placed on a carbon tape and observed under SEM under reduced pressure of 80 Pa. The obtained results are illustrated in FIG. 4 (at a magnification of 500 in FIG. 4A and 5,000 in FIG. 4B).

Figure 4:
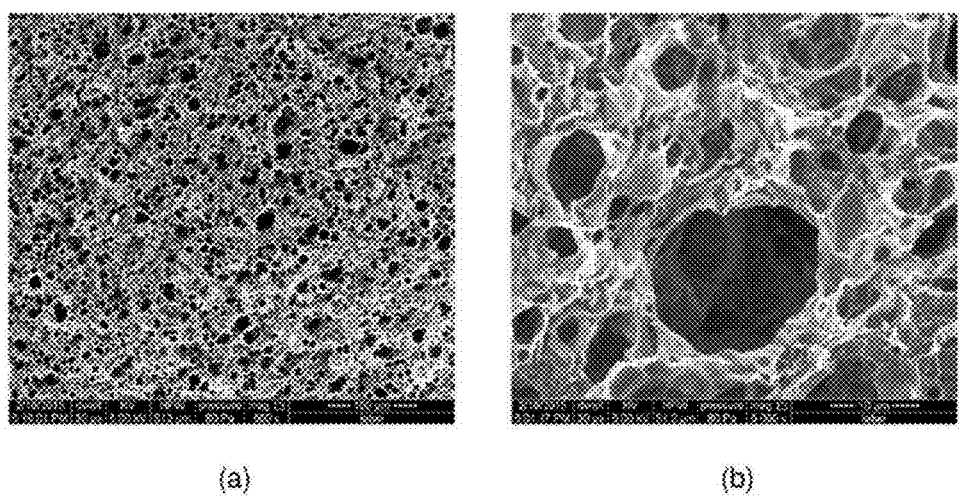
FIG. 4A and FIG. 4B are views illustrating scanning micrographs of a water/KF995 (KF995/water=2/8 (vol/vol)) dispersion gel to which Tween 20 is blended prepared in Example 7 using Compound [8] as a gelator (magnification of FIG. 4A is 500 times and that of FIG. 4B is 5,000 times).

From the SEM images illustrated in FIG. 4, images in which the water-KF995 (KF995/water=2/8 (vol/vol)) dispersion gel containing 1% of Tween 20 formed a sponge like structure having pores were observed. These pores are thought to originate from the dispersed phase formed of the KF995 phase. This suggested the result in which the fibrous structure made of the complex of the gelator (Compound [8]) and the surfactant Tween 20 formed a continuous phase to form the water-oil dispersion gel.

Example 8: Evaluation of Gelation of Ionic Liquid

Gel forming ability for various ionic liquids was evaluated using Compound [8] synthesized in Example 1 as a gelator.

The glucose derivative type gelator (Compound [8]) was poured into a 4 mL screw tube so that the concentration of the gelator reached the predetermined concentration and individual various ionic liquids listed in Table 8 was added thereto, followed by heating the resultant mixture at 100° C. for 30 minutes. The obtained solution was cooled to room temperature and allowed to stand for 1 hour. The formation of gel was determined by turning the screw tube upside down. The results are listed in Table 8.

The ionic liquids (cationic species/anionic species) used in the following Examples are as follows.
<Cationic Species>
EtMeIm: 1-Ethyl-3-methyl-imidazolium ion
BuMeIm: 1-Butyl-3-methyl-imidazolium ion
BuPy: N-butyl pyridinium ion
HeMeIm: 1-Hexyl-3-methyl-imidazolium ion
P13: N-methyl-N-propyl pyrrolidinium ion
TMPA: N, N, N-trimethyl-N-propylammonium ion
<Anionic Species>
TFSI: Bis(trifluoromethylsulfonyl)imide ion
$PF_6$: Hexafluorophosphate ion
I: Iodide ion
$CF_3SO_3$: Trifluoromethanesulfonate ion
$BF_4$: Tetrafluoroborate ion

TABLE 8

Gel forming ability for various ionic liquids

| Ionic liquid | Results of gel formation | Ionic liquid | Results of gel formation |
| --- | --- | --- | --- |
| [EtMeIm][TFSI] | 1 TG | [BuMeIm][$BF_4$] | 5 TG |
| [BuMeIm][TFSI] | 2 TG | [BuPy][TFSI] | 2 TG |
| [BuMeIm][$PF_6$] | 1 TG | [HeMeIm][TFSI] | 2 TG |
| [BuMeIm][I] | 1 * | [P13][TFSI] | 1 G |
| [BuMeIm][$CF_3SO_3$] | 2 TG | [TMPA][TFSI] | 1 TG |

* The color of the ionic liquid itself is dark and the turbidity of the gel cannot be determined.
* The values in the table indicate the concentration (wt %) of the gelator (Compound) required for gelation of each ionic liquid.
* G: Transparent gel and TG: Translucent gel.

As shown in Table 8, the gelator of the present invention was recognized as to be capable of forming the gels of the various ionic liquids.

Figure 5:
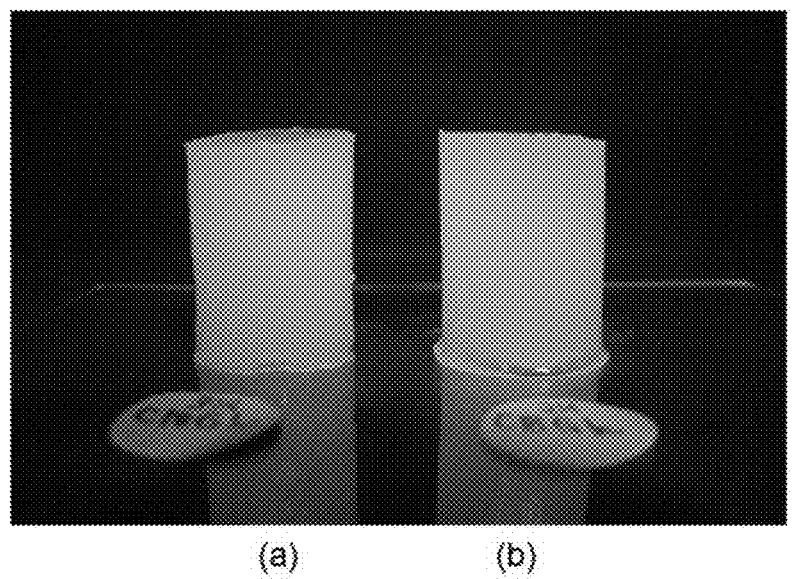
FIG. 5 is a photograph of gels formed from an ionic liquid [BuMeIm][TFSI] to which 3 wt % of Compound [8] is blended (A in FIG. 5) or 2 wt % of Compound [8] is blended (B in FIG. 5).

The gel formed from the ionic liquid [BuMeIm][TFSI] in which the glucose derivative: Compound [8] was blended at 2 wt % or 3 wt % had self-sustainable hardness (a self-supporting property) (refer to FIG. 5: A in FIG. 5 illustrates the gel in which 3 wt % of Compound (8) was blended and B in FIG. 5 illustrates the gel in which 2 wt % of Compound (8) was blended).

Example 9: Measurement of Electric Conductivity

Compound [8] synthesized in Example 1 was used as a gelator and the gelator was added to the ionic liquid [BuMeIm][TFSI] at various concentrations. The resultant mixture was heated at 100° C. for 30 minutes. The obtained solution was poured into the measuring cell of an electric conductivity meter and allowed to stand at room temperature for 1 hour to measure electric conductivity.

The obtained results are listed in Table 9.
Electric Conductivity Measurement Procedure
<Measuring Equipment>
Compact electric conductivity meter LAQUAtwin B-771, manufactured by HORIBA, Ltd.

TABLE 9

Results of Electric conductivity measurement

| Sample state | Liquid | | | Gel | | | |
|---|---|---|---|---|---|---|---|
| Gelator concentration (wt %) | 0 | 0.5 | 1.0 | 2.0 | 3.0 | 4.0 | 5.0 |
| Electric conductivity (mS/cm) | 4.3 | 4.3 | 4.2 | 4.1 | 4.0 | 4.1 | 4.3 |

* The ionic liquid is [BuMeIm][TFSI] and the gelator is Compound [80].

As shown in Table 9, the electric conductivity of the ionic liquid gels obtained by using the gelator of the present invention did not significantly lower and the value of the electric conductivity of the gels were almost equal to that of the ionic liquid (gelator concentration 0 wt %).

Example 10: Ionic Liquid-Oil Dispersion Gel Preparation Test

Into a 4 mL screw thread sample tube, the ionic liquid [BuMeIm][TFSI] and squalane were added at a ratio of 50/50 (vol/vol) and the glucose derivative type gelator (Compound [8]) were poured so that the concentration of the gelator reached 2 wt %. Into another 4 mL screw thread sample tube, the ionic liquid [BuMeIm][TFSI] and squalane were added at a ratio of 50/50 (vol/vol) and Compound [8] as a gelator and Tween 20 were poured so that the concentrations of these components reached 0.25 wt % and 2 wt %, respectively.

The sample tube containing the mixed solution including the gelator was heated for 30 minutes to dissolve the mixed components. Thereafter, shearing was applied using a vortex mixer and, thereafter, the resultant mixture was allowed to stand at room temperature for 1 hour to observe the dispersion state. A state where, after the mixture was allowed to stand to cool, the fluidity of the solution was lost and the solution did not flow down even when the sample tube was turned upside down and where the ionic liquid and squalane were uniformly dispersed was determined to be an "ionic liquid/oil dispersion gel".

The result showed that the ionic liquid/oil dispersion gel (emulsion gel) was capable of being formed in both cases where the gelator [Compound [8]] was used alone and where the gelator and the surfactant (Tween 20) were used in combination in the preparation of the ionic liquid-squalane dispersion gel.

<Identification of Dispersed Phase and Continuous Phase of Ionic Liquid Gel Emulsion Using Confocal Laser Scanning Microscope>

A gel emulsion of [BuMeIm][TFSI]/squalane=50/50 (vol/vol) blended with Rhodamine B containing 2 wt % of Compound [8] was prepared in the same manner as above using 10 μM of Rhodamine B blended ionic liquid [BuMeIm][TFSI]. The gel emulsion was observed with the confocal laser scanning microscope. The obtained result is illustrated in FIG. 6A.

Similarly, a gel emulsion of ionic liquid [BuMeIm][TFSI]/squalane=50/50 (vol/vol) blended with Rhodamine B containing 0.25 wt % of Compound [8] and 2 wt % of Tween 20 as a surfactant was prepared. The obtained gel emulsion was observed with the confocal laser scanning microscope. The obtained result is illustrated in FIG. 6B.

Figure 6:
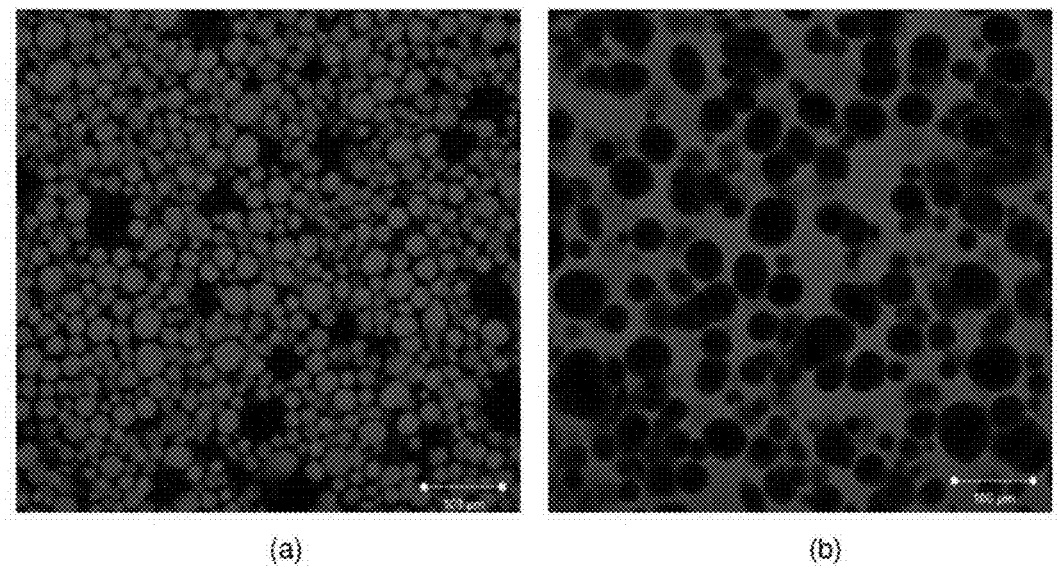
FIG. 6A and FIG. 6B are photographs illustrating confocal laser scanning microscopic images of the gel of ionic liquid [BuMeIm][TFSI]/squalane (ionic liquid/squalane=50/50 (vol/vol)) (FIG. 6A) and the gel of ionic liquid [BuMeIm][TFSI]/squalane (ionic liquid/squalane=50/50 (vol/vol)) (FIG. 6B) to which Tween 20 is further blended prepared in Example 10 using Compound [8] as a gelator.

In FIG. 6, a phase emitting fluorescent color (a phase that appears bright in white) is the ionic liquid phase.

As illustrated in FIG. 6, it was determined that the gel emulsion containing Compound [8] alone formed an ionic liquid/oil (IL/O) gel emulsion (the dispersed phase was the ionic liquid phase and the continuous phase was the squalane phase), whereas the gel emulsion using Compound [8] and Tween 20 in combination formed an oil/ionic liquid (O/IL) gel emulsion (the dispersed phase was the squalane phase and the continuous phase was the ionic liquid phase).

<Measurement of Electric Conductivity of Ionic Liquid Gel Emulsion>

For each of the above gel emulsions of ionic liquid [BuMeIm][TFSI] and squalane in a ratio of 50/50 (vol/vol) formed by blending 2 wt % of Compound [8] or blending 0.25 wt % of Compound [8] and 2 wt % of Tween 20, electric conductivity was measured in accordance with the procedure of [Example 9: Measurement of electric conductivity].

The result showed that the electric conductivity of the gel emulsion containing the gelator (Compound [8]) alone was 0 μS/cm, whereas the electric conductivity of the gel emulsion when the gelator and the surfactant (Tween 20) were used in combination was 1.67 mS/cm.

Together with the observation result of the confocal laser scanning microscope, it was determined that the gel emulsion including Compound [8] alone having an electric conductivity of 0 μS/cm was an IL/O emulsion, so that the electric conduction property due to the ionic liquid was shielded. On the other hand, it was determined that the gel emulsion including Compound [8] and Tween 20 was the O/IL emulsion and showed an electric conduction property (1.67 mS/cm) even in the gel emulsion state.

Example 11: Gel Forming Ability Test in Fine Particle Dispersion System (1)

The gel forming ability in the fine particle dispersion system was evaluated using Compound [8] prepared in Synthesis Example 1 as a gelator.

As the fine particles, silicone-treated (methyl hydrogen polysiloxane-treated) powders (trade name: Talc DN-SH, Titanium DN-SH (2) (fine particle component: titanium oxide), and Sericite DN-MC (2) (fine particle component: mica), DN-HAP (SH) (fine particle component: hydroxyapatite), all products were manufactured by Dainihon Kasei Co., Ltd.) were used.

Into a screw thread sample tube, Compound [8] (10 mg or 20 mg) prepared in Synthesis Example 1 as a gelator, the above various fine particles (50 mg, or 50 mg or 100 mg in the case of Titanium DN-SH (2)), and KF995 (1 mL) were poured. After the resultant mixture was heated at 80° C. for 30 minutes, the sample tube was allowed to cool for 1 hour at room temperature. The formation of gel was determined by turning the screw tube upside down. The results are listed in Table 10.

TABLE 10

Results of fine particle dispersion gel formation (1)

| Gelator concentration | Type of fine particles | Possibility of gelation |
|---|---|---|
| 2 wt % (20 m) | Talc DN-SH | Possible |
| 1 wt % (10 mg) | | Possible |

TABLE 10-continued

Results of fine particle dispersion gel formation (1)

| Gelator concentration | Type of fine particles | Possibility of gelation |
|---|---|---|
| 2 wt % (20 mg) | Titanium DN-SH(2) | Possible |
| 1 wt % (10 mg) | | Possible |
| 2 wt % (20 mg) | | Possible * |
| 1 wt % (10 mg) | | Possible * |
| 2 wt % (20 mg) | Sericite DN-MC(2) | Possible |
| 1 wt % (10 mg) | | Possible |
| 2 wt % (20 mg) | DN-HAP (SH) | Possible |
| 1 wt % (10 mg) | | Possible |

The mark "*" indicates the result when 100 mg of Titanium DN-SH (2) was added.

As shown in Table 10, it was determined that gelation was also possible even in the system in which the various fine particles were dispersed.

Example 12: Gel Forming Ability Test in Fine Particle Dispersion System (2)

Into a screw thread sample tube, Compound [8] (40 mg) as a gelator; KF995 (1 mL); and water, an L-ascorbic acid aqueous solution (20% of an aqueous solution), an L-ascorbic acid 2-phosphate trisodium salt aqueous solution (40% of an aqueous solution), or a glycine aqueous solution (18% of an aqueous solution) (each of the materials was poured in an amount of 1 mL) were poured to prepare a sample. In addition, silicone-treated fine particles Titanium DN-SH (2) (100 mg or 200 mg) was further added to prepare samples (a ratio of KF995 and the aqueous media such as water: 50/50 (vol/vol)). Each of the obtained samples was heated at 80° C. for 30 minutes and subsequently shaken with a vortex mixer for 3 minutes. Thereafter, the resultant mixture was allowed to cool for 1 hour at room temperature to determine formation of gels. The results are listed in Table 11.

TABLE 11

Results of fine particle dispersion gel formation (2)

| Aqueous medium | Presence of fine particles | Possibility of gelation |
|---|---|---|
| Water | Absence | Possible |
| | Presence | Possible |
| | Presence * | Possible |
| 20% of Ascorbic acid aqueous solution | Absence | Possible |
| | Presence | Possible |
| | Presence * | Possible |
| 40% of Ascorbic acid phosphate sodium salt aqueous solution | Absence | Possible |
| | Presence | Possible |
| | Presence * | Possible |
| 18% of Glycine aqueous solution | Absence | Possible |
| | Presence | Possible |
| | Presence * | Possible |

The mark "*" indicates the result when 200 mg of titanium DN-SH (2) was used.

As shown in Table 11, it was determined that gel emulsion formation was possible in any of the systems.

Example 13: Gel Forming Ability Test in Fine Particle Dispersion System (3)

Preparation of a high internal phase ratio gel emulsion (emulsion having a very large volume fraction of dispersed phase) was examined when the ratio of KF995 and water was set to 20/80 (vol/vol).

Into a screw thread sample tube, Compound [8] (10 mg) as a gelator; KF995 (0.4 mL); water, an L-ascorbic acid aqueous solution (20% of an aqueous solution), an L-ascorbic acid 2-phosphate trisodium salt aqueous solution (40% of an aqueous solution), or a glycine aqueous solution (18% of an aqueous solution) (each of the materials was poured in an amount of 1.6 mL); and silicone-treated fine particles Titanium DN-SH (2) (100 mg or 200 mg) and Span 80 (10 mg) were poured to prepare a sample (only in the case of water, a sample to which Span 80 was not blended was prepared). Each of the obtained samples was heated at 80° C. for 30 minutes and subsequently shaken with a vortex mixer for 3 minutes. Thereafter, the resultant mixture was allowed to cool for 1 hour at room temperature to determine formation of gels. The results are listed in Table 12.

TABLE 12

Results of fine particle dispersion gel formation (3)

| Aqueous medium | Presence of Span 80 | Possibility of gelation |
|---|---|---|
| Water | Absence | Impossible |
| | Presence | Possible |
| | Presence * | Possible |
| 20% of Ascorbic acid aqueous solution | Presence | Possible |
| | Presence * | Possible |
| 40% of Ascorbic acid phosphate sodium salt aqueous solution | Presence | Possible |
| | Presence * | Possible |
| 18% of Glycine aqueous solution | Presence | Possible |
| | Presence * | Possible |

The mark "*" indicates the result when 200 mg of Titanium DN-SH (2) was added.

As shown in Table 12, it was determined that in the system in which the ratio of KF995 and the aqueous medium was 20/80 (vol/vol), high internal phase ratio gel emulsions were capable of being prepared by blending Span 80.

<Observation of Fine Particle Dispersion Gel Using Confocal Laser Scanning Microscope>

A gel emulsion of KF995/water=20/80 (vol/vol) prepared by blending 0.5 wt % of Compound [8] as a gelator, 0.5 wt % of Span 80, and 5 wt % of the silicone-treated fine particles Titanium DN-SH (2) was observed with the confocal laser scanning microscope. The obtained result is illustrated in FIG. 7.

From the results of above <Water-KF995 dispersion gel preparation test> and <Identification of dispersed phase and continuous phase of dispersion gel using confocal laser scanning microscope> in [Example 6], it has been determined that the water-KF995 dispersion gel blended with Span 80 formed the W/O emulsion (the dispersed phase is the aqueous phase and the continuous phase is the KF995 phase).

Figure 7:
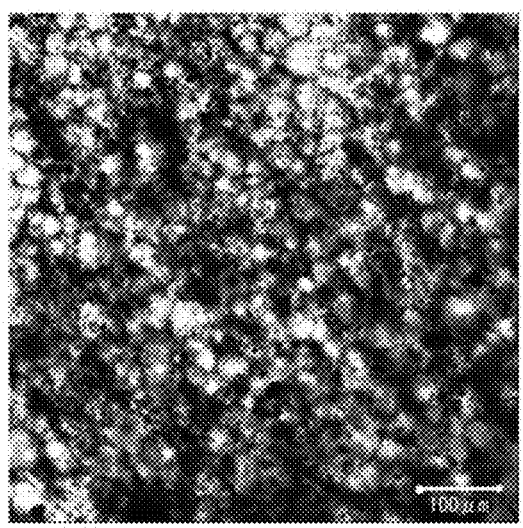
FIG. 7 is a photograph illustrating a confocal laser scanning microscopic image of the gel of KF995/water=20/80 (vol/vol) to which titanium and Span 80 are blended prepared in Example 13 using Compound [8] as a gelator.

As shown in FIG. 7, the titanium fine particles were determined to be dispersed in the continuous phase (KF995 phase).

Example 14: Preparation of Foundation

In accordance with the following Table 13, the whole amount of Component (A) was stirred and mixed for 15 minutes with an automatic mortar (Type ANM-1000, manufactured by NITTO KAGAKU CO., Ltd.). Except for Compound [8], every material used in the test was purchased from Orange Flower Co., Ltd. and these materials were used. Thereafter, each of Components (B) (Formulation 1 to Formulation 3 were heated and melted) prepared by stirring and mixing in advance was added and the resultant mixture was further mixed for 15 minutes. The obtained powder was poured into a compact case (model number: cp-23, manufacturer: Orange Flower Co., Ltd.) and the powder was compacted using a flat plate.

Figure 8:
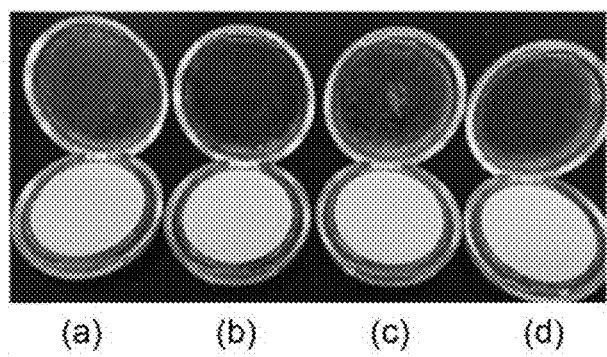
FIG. 8 is a photograph illustrating appearance of foundations prepared in Example 14.

The appearance of the foundation obtained by putting the foundation in the compact case is illustrated in FIG. 8. FIG. 8 illustrates (a) Comparative Formulation, (b) Formulation 1, (c) Formulation 2, and (d) Formulation 3.

TABLE 13

Foundation formulation

| Component (A)/g | | Component (B)/g | | | |
|---|---|---|---|---|---|
| | | Comparative Formulation | Formulation 1 | Formulation 2 | Formulation 3 |
| Sericite | 8.0 | — | — | — | — |
| Mica | 1.0 | — | — | — | — |
| Titanium dioxide | 1.2 | — | — | — | — |
| Anhydrous silicic acid | 1.0 | — | — | — | — |
| Talc | 6.9 | — | — | — | — |
| Yellow iron oxide | Adequate amount *1 | — | — | — | — |
| Black iron oxide | Adequate amount *1 | — | — | — | — |
| Red iron oxide | Adequate amount *1 | — | — | — | — |
| Squalane | — | 0.8 | 0.8 | 0.8 | 0.8 |
| Aqua jojoba oil | — | 0.8 | 0.8 | 0.8 | 0.8 |
| Sorbitan oleate | — | 0.3 | — | — | — |
| Compound [8] | — | — | 0.008 | 0.016 | 0.032 |

*1 The total amount of yellow iron oxide, black iron oxide, and red iron oxide is 0.3 g.

As shown in FIG. 8, it was determined that the foundations were produced in any of Comparative Formulation and Formulation 1 to Formulation 3. In particular, in the foundations of Formulation 1 to Formulation 3, it was determined that various blended powder and oil mixed were uniformly dispersed. Among them, the result that has suggested that Formulation 1 and Formulation 2 not only have a good molding property but also give a moist feeling of use was obtained.

The invention claimed is:

1. A gelator comprising a compound of Formula (1) or Formula (2):

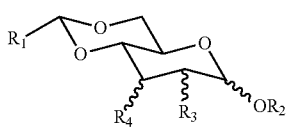
(1)

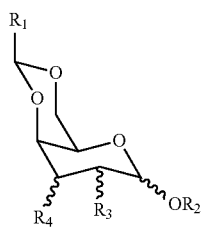
(2)

wherein
$R_1$ is a linear or branched alkyl group having a carbon atom number of 9 to 20, a cyclic alkyl group having a carbon atom number of 13 to 20, or a linear or branched alkenyl group having a carbon atom number of 9 to 20;

$R_2$ is a hydrogen atom, a linear or branched alkyl group having a carbon atom number of 1 to 10, or an aryl group optionally having a substituent; and $R_3$ and $R_4$ are hydroxy groups.

2. The gelator according to claim 1, wherein the compound of Formula (1) is a compound of Formula (3):

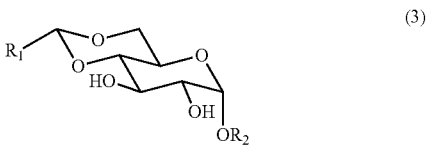
(3)

wherein $R_1$ and $R_2$ have the same meanings as defined in Formula (1).

3. The gelator according to claim 1, wherein the compound of Formula (1) is a compound of Formula (4):

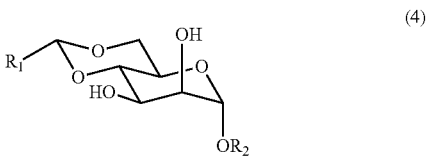
(4)

wherein $R_1$ and $R_2$ have the same meanings as defined in Formula (1).

4. A gel comprising:
the gelator as claimed in claim 1; and
a hydrophobic organic solvent, a hydrophilic organic solution, a hydrophobic organic solution, or an aqueous solution.

5. A gel comprising:
the gelator as claimed in claim 1;
a surfactant; and
a hydrophobic organic solvent, a hydrophilic organic solvent, water, a hydrophilic organic solution, a hydrophobic organic solution, or an aqueous solution.

6. The gel according to claim 4, wherein the hydrophobic organic solvent is at least one solvent selected from the group consisting of vegetable oils, esters, silicone oils, and hydrocarbons.

7. The gel according to claim 4, wherein the hydrophobic organic solution is a mixed solvent of water and the hydrophobic organic solvent wherein the hydrophobic organic solvent is at least one solvent selected from the group consisting of vegetable oils, esters, silicone oils, and hydrocarbons.

8. The gel according to claim 5, wherein the hydrophilic organic solvent is at least one solvent selected from the group consisting of methanol, ethanol, 2-propanol, i-butanol, pentanol, hexanol, 1-octanol, iso-octanol, acetone, cyclohexanone, acetonitrile, dioxane, glycerol, propylene glycol, ethylene glycol, and dimethyl sulfoxide.

9. The gel according to claim 4, wherein the hydrophilic organic solution is a mixed solvent of water and the hydrophilic organic solvent wherein the hydrophilic organic solvent is at least one solvent selected from the group consisting of methanol, ethanol, 2-propanol, i-butanol, pentanol, hexanol, 1-octanol, iso-octanol, acetone, cyclohexanone, acetonitrile, dioxane, glycerol, propylene glycol, ethylene glycol, and dimethyl sulfoxide.

10. The gel according to claim 4, wherein fine particles are further dispersed in the gel.

11. The gelator according to claim 1, wherein the gelator is a gelator of an ionic liquid.

12. A gel comprising:

the gelator as claimed in claim 1, and an ionic liquid.

13. A cosmetic base material or a medical base material comprising the gelator as claimed in claim 1.

14. A method for producing the compound of Formula (1) or Formula (2) as claimed in claim 1, the method being characterized by comprising:

producing the compound of Formula (1) or Formula (2) by annelation reaction of a compound of a formula $R_1$—CHO (wherein $R_1$ is a linear or branched alkyl group having a carbon atom number of 9 to 20, a cyclic alkyl group having a carbon atom number of 13 to 20, or a linear or branched alkenyl group having a carbon atom number of 9 to 20) with glucose, mannose, galactose, or a derivative thereof in a single pot in the presence of triethyl orthoformate, DMF, or p-toluenesulfonic acid.

15. A compound of Formula (7) or Formula (8):

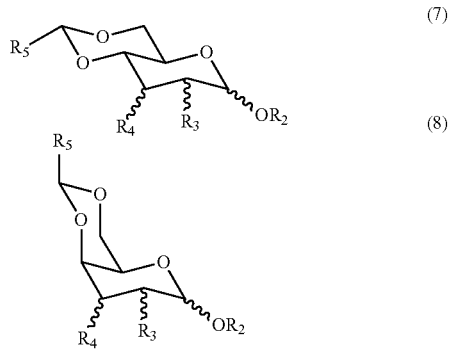

wherein $R_5$ is a linear or branched alkyl group having a carbon atom number of 13 to 20, a cyclic alkyl group having a carbon atom number of 13 to 20, or a linear or branched alkenyl group having a carbon atom number of 13 to 18;

$R_2$ is a hydrogen atom, a linear or branched alkyl group having a carbon atom number of 1 to 10, or an aryl group optionally having a substituent; and $R_3$ and $R_4$ are hydroxy groups.

* * * * *